(12) United States Patent
Potyrailo et al.

(10) Patent No.: US 11,977,025 B2
(45) Date of Patent: May 7, 2024

(54) SYSTEM AND METHOD FOR ON-BOARD DATA ANALYSIS FOR MULTI-GAS SENSING

(71) Applicant: General Electric Company, Schenectady, NY (US)

(72) Inventors: Radislav Alexandrovich Potyrailo, Niskayuna, NY (US); Baokai Cheng, Schenectady, NY (US); Aghogho Atemu Obi, Weston, FL (US); Christopher Collazo-Davila, Clifton Park, NY (US); Richard Jean-Luc St. Pierre, Clifton Park, NY (US)

(73) Assignee: GE INFRASTRUCTURE TECHNOLOGY LLC, Greenville, SC (US)

( * ) Notice: Subject to any disclaimer, the term of this patent is extended or adjusted under 35 U.S.C. 154(b) by 125 days.

(21) Appl. No.: 17/859,904

(22) Filed: Jul. 7, 2022

(65) Prior Publication Data

US 2024/0011900 A1 Jan. 11, 2024

(51) Int. Cl.
*G01N 21/3504* (2014.01)
*G01N 33/00* (2006.01)

(52) U.S. Cl.
CPC ..... *G01N 21/3504* (2013.01); *G01N 33/0006* (2013.01); *G01N 2201/0221* (2013.01)

(58) Field of Classification Search
CPC ........... G01N 21/3504; G01N 33/0006; G01N 2201/0221
See application file for complete search history.

(56) References Cited

U.S. PATENT DOCUMENTS 6,422,823 B2 7/2002 Bernard et al.
8,211,035 B2 7/2012 Melker et al.
(Continued)

FOREIGN PATENT DOCUMENTS

CN 104678061 A 6/2015

OTHER PUBLICATIONS

Marco et al. (Signal and Data Processing for Machine Olfaction and Chemical Sensing: A Review, IEEE Sensors Journal, vol. 12, No. 11, Nov. 2012) (Year: 2012).*

(Continued)

*Primary Examiner* — David P Porta
*Assistant Examiner* — Meenakshi S Sahu
(74) *Attorney, Agent, or Firm* — Fletcher Yoder, P.C.

(57) ABSTRACT

Gas sensors are disclosed having an on-board, low-power data processor that uses multivariable gas classification and/or gas quantitation models to perform on-board data processing to resolve two or more gases in a fluid sample. To reduce computational complexity, the gas sensor utilizes low-power-consumption multivariable data analysis algorithms, inputs from available on-board sensors of ambient conditions, inputs representing contextual data, and/or excitation responses of a gas sensing material to select suitable gas classification and/or gas quantitation models. The data processor can then utilize these gas classification and quantitation models, in combination with measured dielectric responses of a gas sensing material of the gas sensor, to determine classifications and/or concentrations of two or more gases in a fluid sample, while consuming substantially less power than would be consumed if a global comprehensive model were used instead. Thus, the data processor is utilized for linear, nonlinear, and non-monotonic multivariate regressions.

19 Claims, 12 Drawing Sheets

(56) References Cited

U.S. PATENT DOCUMENTS

| | | | |
|---|---|---|---|
| 8,936,191 | B2 | 1/2015 | Potyrailo et al. |
| 9,147,144 | B2 | 9/2015 | Potyrailo et al. |
| 9,389,260 | B2 | 7/2016 | Potyrailo et al. |
| 10,157,530 | B2 | 12/2018 | Parra et al. |
| 10,241,095 | B2 | 3/2019 | Coates |
| 10,368,146 | B2 | 7/2019 | Potyrailo et al. |
| 10,746,680 | B2 | 8/2020 | Potyrailo et al. |
| 10,812,878 | B2 | 10/2020 | Potyrailo et al. |
| 10,813,562 | B2 | 10/2020 | Moon et al. |
| 10,817,530 | B2 | 10/2020 | Siebel et al. |
| 10,820,862 | B2 | 11/2020 | Rogers et al. |
| 10,966,657 | B2 | 4/2021 | Potyrailo et al. |
| 2021/0072175 | A1 | 3/2021 | Potyrailo et al. |

OTHER PUBLICATIONS

Menciassi, "Bioelectronic Devices: Gut-powered ingestible biosensors," vol. 1, Article No. 0050, Mar. 9, 2017, Nature Biomedical Engineering, DOI: 10.1038/s41551-017-0050 , 2 Pages.

Yun et al., "Ultrasensitive and Highly Selective Graphene-Based Single Yarn for Use in Wearable Gas Sensor," Jun. 4, 2015, Scientific Reports, 5:10904, DOI: 10.1038/srep10904 , 7 Pages.

Ataman et al., "A robust platform for textile integrated gas sensors," Sensors and Actuators B 177, Dec. 6, 2012, pp. 1053-1061.

Li et al., "Low power Multi-mode Electrochemical Gas Sensor Array System for Wearable Health and Safety Monitoring," Sensors-9854-2014.R1, Jun. 17, 2014, 8 pages.

Kalantar-Zadeh et al., "A human pilot trial of ingestible electronic capsules capable of sensing different gases in the gut," nature electronics, vol. 1, Jan. 2018, https://doi.org/10.1038/s41928-017-0004-x , pp. 79-87.

Singh et al., "Flexible Graphene-Based Wearable Gas and Chemical Sensors," Sep. 6, 2017, American Chemical Society, Applied Materials & Interfaces, DOI: 10.1021/acsami.7b07063 , pp. 34544-34586.

Nikolic et al., "Semiconductor Gas Sensors: Materials, Technology, Design, and Application," Nov. 23, 2020, Sensors, Belgrade, Serbia, 30 pages.

Dai et al., "Printed Gas Sensors," Feb. 17, 2020, Chem. Soc. Rev., 2020, 49, pp. 1756-1789.

Nasiri et al., "Progress and challenges in fabrication of wearable sensors for health monitoring," May 29, 2020, Sensors and Actuators A 312 (2020) 112105, https://doi.org/10.1016/j.sna.2020.112105 , 17 Pages.

Potyrailo et al., Multianalyte Chemical Identification and Quantitation Using a Single Radio Frequency Identification Sensor, Analytical Chemistry, vol. 79, No. 1, Jan. 1, 2007, pp. 45-51.

Potyrailo et al., "Morpho butterfly wing scales demonstrate highly selective vapour response," Feb. 1, 2007, Nature Photonics, vol. 1, pp. 123-128.

Potyrailo et al., "Materials and Transducers Toward Selective Wireless Gas Sensing," Nov. 9, 2011, Chem Rev., doi:10.1021/cr2000477. , 99 Pages.

Potyrailo et al., "Battery-free Radio Frequency Identification (RFID) Sensors for Food Quality and Safety," Aug. 10, 2012, Journal Agricultural and food chemistry, dx.doi.org/10.1021/jf30241 , pp. 8535-8543.

Potyrailo et al., "Towards outperforming conventional sensor arrays with fabricated individual photonic vapour sensors inspired by Morpho butterflies," Sep. 1, 2015, Nature communications, DOI: 10.1038/ncomms8959 , 12 Pages.

Potyrailo, "Multivariable Sensors for Ubiquitous Monitoring of Gases in the Era of Internet of Things and Industrial Internet," Mar. 19, 2016, Chemical Reviews, DOI: 10.1021/acs.chemrev.6b00187 , 47 Pages.

Potyrailo et al., "Multivariable Electrical Resonant Sensors for Independent Quantitation of Aging and External Contaminants in Lubricating Oils," IEEE Sensors Journal, vol. 19, No. 4, Feb. 15, 2019, pp. 1542-1553.

Potyrailo et al., "Label-free independent quantitation of viable and non-viable cells using a multivariable multi-resonant sensor," Oct. 10, 2018, Bioelectrochemistry 125 (2019), https://doi.org/10.1016/j.bioelechem.2018.10.001 , pp. 97-104.

Potyrailo et al., "Extraordinary performance of semiconducting metal oxide gas sensors using dielectric excitation," Nature Electronics, 2020, https://doi.org/10.1038/s41928-020-0402-3 , 59 Pages.

Potyrailo et al., "Multi-gas sensors based on dielectric excitation," GE Research, https://web.archive.org/web/20200812161514/https://www.ge.com/research/project/multi-gas-sensors-based-dielectric-excitation , Last accessed Oct. 5, 2022, 5 Pages.

Lee, "Linear gas sensing with dielectric excitation," May 2020, vol. 3, Nature Electronics, pp. 239-240.

* cited by examiner

SYSTEM AND METHOD FOR ON-BOARD DATA ANALYSIS FOR MULTI-GAS SENSING

STATEMENT REGARDING FEDERALLY SPONSORED RESEARCH & DEVELOPMENT

This invention was made with Government support under contract awarded by Centers for Disease Control and Prevention. The Government has certain rights in the invention.

BACKGROUND

The subject matter disclosed herein generally relates to gas sensing, and more specifically relates to gas sensing using metal oxide semiconductor (MOS) sensors.

Metal oxide semiconductor (MOS) sensors can be operated as chemiresistors and are popular because of their ability to non-selectively detect numerous gases with the proper selection of the base semiconductor material and doping materials. In such gas-responsive chemiresistor, a change in resistance of the MOS sensing element is measured, and this change in resistance is proportional to the gas concentrations in a fluid sample. However, the limited selectivity of MOS gas-responsive chemiresistor has hindered the use of such sensor in certain multi-gas sensing applications.

For a gas sensing system, measurements performed by the gas sensor are processed to resolve gases in a fluid sample. For example, a gas sensor may provide one or more measurements to an external computing system, such as a server or a cloud-computing system, for processing. While the external computing system may have superior processing resources to more quickly process the measurements, it is presently recognized that this approach includes drawbacks. For example, it is recognized that communicating the measurements from the gas sensor to the external computing system consumes considerable power, and that communication between the gas sensor and the external computing system may be slow and/or intermittently interrupted.

BRIEF DESCRIPTION

With the foregoing in mind, present embodiments are directed to gas sensor having an on-board, low-power data processor that uses multivariable gas classification and/or gas quantitation models to perform on-board data processing to resolve two or more gases in a fluid sample. It is presently recognized that data processors for multivariate analysis of multi-gas-sensing data have a significant trade-off between a desired high performance (e.g., a desired accuracy of predicted gas classifications and concentrations) and a desire to minimize power consumption for the data processing that determines the predicted gas classifications and concentration. It is further recognized that this data processing trade-off imposes a substantial barrier that has prevented the adoption of gas sensors to new emerging applications ranging from industrial safety, to asset monitoring, to process monitoring, and to wearable, textile-integrated, ingested, or tattooed unobtrusive systems. As such, present embodiments are directed to gas sensors that provide a technical solution for achieving a desired accuracy of predicted gas classifications and concentrations, while minimizing power consumption of the data processor when determining these predicted gas classifications and concentrations.

To reduce the computational complexity (and thus the power consumption of the data processor), present embodiments utilize relatively low-power-consumption multivariable data analysis algorithms, inputs from available on-board sensors of ambient conditions (e.g. ambient temperature, humidity, pressure), and/or inputs representing contextual data (e.g. location, surroundings) associated with the multi-gas analysis being performed. Based on these inputs, the on-board, low-power data processor of the gas sensor selects suitable gas classification and/or gas quantitation models from a stored library of models, which are generally less complex than corresponding global comprehensive models. The data processor can then utilize these gas classification and quantitation models, in combination with measured dielectric responses of a gas sensing material of the gas sensor, to determine classifications and/or concentrations of two or more gases in a fluid sample, while consuming substantially less power than would be consumed if a global comprehensive model were used instead. Thus, the data processor is utilized for linear, nonlinear, and non-monotonic multivariate regressions. In some embodiments, the power consumed by the data processor when resolving gases in the fluid sample is less that the power that would be consumed for the gas sensor to power a radio-frequency (RF) communication device (e.g., to provide the measurements to an external computing system for data processing). In some embodiments, the power consumed by the data processor when resolving gases in the fluid sample is less that the power that would be consumed by the gas sensing element.

In one embodiment, a gas sensor for multi-gas analysis of a fluid sample includes a gas sensing element configured to contact the fluid sample; a measurement circuit operatively coupled to the gas sensing element and configured to provide dielectric excitation to, and to measure dielectric excitation responses of, the gas sensing element while the gas sensing element contacts the fluid sample; and data processing unit communicatively coupled to the measurement circuit, wherein the data processing unit comprises a memory storing gas analysis models and an on-board, low-power data processor. The on-board, low-power data processor is configured to resolve at least two gases in the fluid sample by: receiving, from the measurement circuit, the dielectric excitation responses of the gas sensing element while the gas sensing element contacts the fluid sample; determining contextual data associated with the multi-gas analysis of the fluid sample; selecting, from the memory, at least one of the gas analysis models stored in the memory based, at least in part, on the received dielectric excitation responses of the gas sensing element, the determined contextual data, or any combination thereof; selecting and providing, as inputs to the at least one selected gas analysis model, at least a portion of the received dielectric excitation responses to determine outputs of the at least one selected gas analysis model; and determining a respective classification, or a respective concentration, or a combination thereof, for the at least two gases in the fluid sample based on the outputs of the at least one selected gas analysis model.

In one embodiment, a method of operating an on-board, low-power data processor of a gas sensor for multi-gas analysis of a fluid sample includes: receiving, from a measurement circuit of the gas sensor operably coupled to a gas sensing element of the gas sensor, dielectric excitation responses of the gas sensing element while the gas sensing element is exposed to the fluid sample; receiving, from at least one ambient sensor of the gas sensor, ambient environmental data associated with the multi-gas analysis of the fluid sample; and receiving, from an input device of the gas sensor, contextual data associated with the multi-gas analysis of the fluid sample. The method includes: selecting, from a memory associated with the on-board, low-power data processor, one or more gas analysis models based on the received dielectric excitation responses of the gas sensing element, the received ambient environmental data, or the received contextual data, or any combination thereof; selecting and providing, as inputs to the one or more selected gas analysis models, at least a portion of the received dielectric excitation responses to determine outputs of the one or more selected gas analysis models; and determining a respective classification, or a respective concentration, or a combination thereof, of at least two gases in the fluid sample based on the outputs of the one or more selected gas analysis models.

In one embodiment, a gas sensor for multi-gas analysis of a fluid sample includes a gas sensing element configured to contact the fluid sample; a measurement circuit operatively coupled to the gas sensing element and configured to provide dielectric excitation to, and to measure dielectric excitation responses of, the gas sensing element while the gas sensing element contacts the fluid sample; an ambient environment sensor configured to collect ambient environmental data of an ambient environment associated with the multi-gas analysis; an input device configured to receive contextual data associated with the multi-gas analysis; and data processing unit communicatively coupled to the measurement circuit, the ambient environment sensor, and the input device. The data processing unit comprises a memory storing gas analysis models and an on-board, low-power data processor configured to resolve at least two gases in the fluid sample by: receiving, from the measurement circuit, the dielectric excitation responses of the gas sensing element while the gas sensing element contacts the fluid sample; receiving, from the input device, the contextual data associated with the multi-gas analysis of the fluid sample; receiving, from the ambient environment sensor, the ambient environmental data associated with the multi-gas analysis of the fluid sample; selecting, from the memory, at least one of the gas analysis models stored in the memory based at least in part on the received dielectric excitation responses of the gas sensing element, the received contextual data, or the received ambient environmental data, or any combination thereof; selecting and providing, as inputs to the at least one selected gas analysis model, at least a portion of the received dielectric excitation responses to determine outputs of the at least one selected gas analysis model; and determining a respective classification, or a respective concentration, or a combination thereof, for the at least two gases in the fluid sample based on the outputs of the at least one selected gas analysis model.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
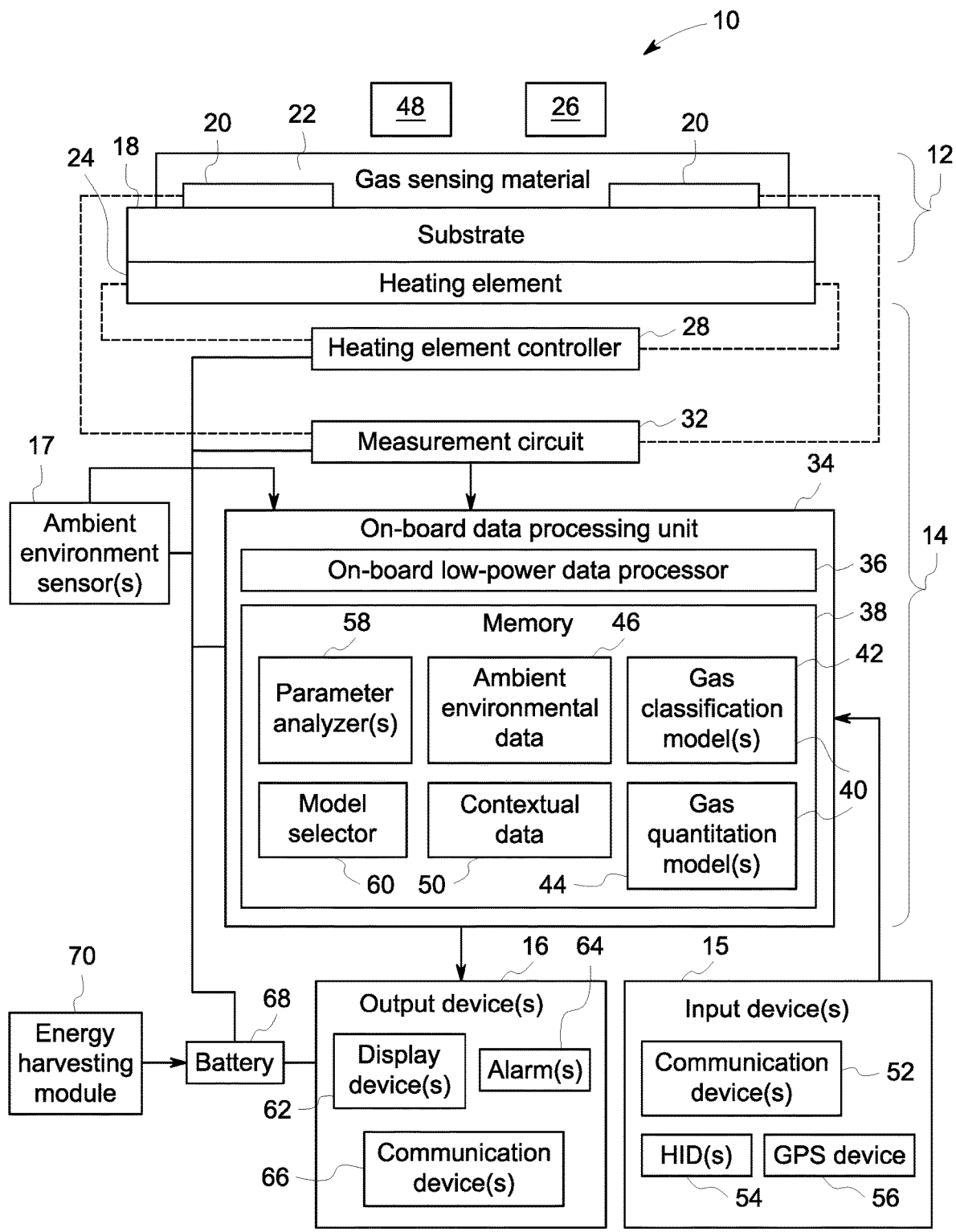
FIG. 1 is a schematic diagram of an embodiment of a gas sensor for multi-gas analysis of fluid samples, in accordance with aspects of the present technique.

Present embodiments are directed to a system and a method for multi-gas sensing using dielectric excitation of a metal oxide semiconductor sensing material arranged as a gas sensing element. It may be noted that metal oxide semiconductor sensing materials are often abbreviated in the industry as metal oxide semiconductor (MOS) materials or semiconducting metal oxide (SMOX) or semiconducting metal oxide (MOX) materials. Traditional MOS-based gas sensors measure only a direct current (DC) resistance response. A measurement of a single response per sensor under a given excitation condition is known as a single-output readout and the sensor is known as a single-output sensor. To resolve multiple gases in a fluid sample, traditional MOS-based gas sensors measure DC resistance responses at several different temperatures.

However, it is presently recognized that, by measuring dielectric excitation responses of the gas sensing material, enhanced multi-gas selectivity and resolution can be achieved using fewer operating temperatures than would be used by the same MOS gas sensing material configured to perform multi-gas resolution based on resistance responses alone. Additionally, the disclosed gas sensors and gas sensing techniques enable improved response linearity, improved dynamic range, and reduced computational resource consumption for multi-gas quantitation relative to traditional resistance-based gas sensing methods. Furthermore, by reducing the number of operating temperature switching events, present embodiments enable gas sensors with improved measurement quality and enhanced operational lifetimes. That is, it is presently recognized that, using a set of predetermined operating temperatures, the impedance spectrum of a gas sensing material is differently affected by different gases, and such desired differences are more pronounced as compared to the resistance response of the same gas sensing material, even when additional operating temperatures are used. Thus, present embodiments unexpectedly demonstrate MOS-based gas sensors that can discriminate or differentiate between different gases using responses collected using at least one operating temperature, wherein this differentiation is superior in the resolution between different gases and in baseline stability, as compared to the resistance response of the same gas sensing material at more than one operating temperatures.

As noted above, traditional MOS-based gas sensors typically measure DC resistance responses of a gas sensing material at several different operating temperatures when performing multi-gas analysis of a fluid sample. In contrast, present embodiments of gas sensors include a MOS-based gas sensing material that interacts with gases in a fluid sample at one or more operating temperatures and provides excitation responses to particular dielectric excitation frequencies, wherein these dielectric excitation responses of the gas sensing material are measured and analyzed to resolve two or more gases in a fluid sample. As used herein, the terms "analyte", "analyte gas", or "analyte fluid" refer to a component of interest in the measured fluid. As used herein, the term "interferent", "interference gas", "interference fluid" refers to any component in the measured fluid that can undesirably affect the accuracy and precision of measurements of the analyte with the sensor.

With the foregoing in mind, FIG. 1 is a schematic diagram of an embodiment of a gas sensor 10 for multi-gas analysis of fluid samples, in accordance with the present technique. In different embodiments, the gas sensor 10 may be a wearable gas sensor, an ingestible gas sensor, or a tattooed gas sensor for personal (e.g., patient) monitoring. In certain embodiments, the gas sensor 10 may be an industrial environmental sensor, an asset monitoring sensor, an industrial process monitoring gas sensor, a consumer sensor, a transportation sensor, a security sensor, or any combination thereof.

For the embodiment illustrated in FIG. 1, the gas sensor 10 generally includes at least one gas sensing element 12, control circuitry 14, one or more input devices 15, one or more output devices 16, and one or more ambient environment sensors 17. Each gas sensing element 12 includes a substrate 18 having sensing electrodes 20 disposed thereon, as well as a gas sensing material 22 (e.g., a suitably formulated metal oxide semiconductor material (MOS) applied to form a gas sensing film) disposed on the substrate 18 between the sensing electrodes 20. In certain embodiments, the gas sensor 10 may include multiple gas sensing elements 12 (e.g., an array of gas sensing elements 12), such as gas sensing elements having different MOS-based gas sensing materials 22 and/or operating at different temperatures. In certain embodiments, there may be more than two sensing electrodes 20, and the sensing electrodes 20 may include a plurality of interdigitated sensing electrodes. It may be appreciated that the gas sensing material 22 is generally applied onto the electrodes 20 to form the gas sensing film, such that the dielectric excitation of the gas sensing material 22, as well as the measurement of the dielectric excitation responses of the gas sensing material 22, is performed via the electrodes 20.

Additionally, a resistive heating element 24 is disposed on a surface of the substrate 18, opposite the gas sensing material 22, and is designed to heat the gas sensing material 22 to at least one suitable operating temperature during multi-gas analysis of a fluid sample 26. In certain embodiments, the heating element 24 may be disposed on a surface of the substrate 18 that is opposite the gas sensing material 22, while in other embodiments, the heating element 24 may be disposed on the same surface of the substrate 18 as the gas sensing material 22. For embodiments with multiple gas sensing elements 12, in certain cases, more than one gas sensing material 22 may be applied to a common substrate to form the multiple gas sensing elements 12 on a common substrate 18, which may be heated by a single heating element, while in other cases, each gas sensing material 22 may be disposed on a respective substrate 18 with a respective heating element 24. Additionally, in certain embodiments, the heating element 24 may be integrated into the substrate 18 as a monolithic structure.

During operation of the gas sensor 10, the gas sensing material 22 of the gas sensing element 12 is heated to one or more operating temperatures as the gas sensing material 22 is exposed to the fluid sample 26, which may include two or more gases (e.g., an analyte gas and an interferent gas, at least two analyte gases). As such, the control circuitry 14 of the illustrated gas sensor 10 includes a heater controller 28 that is electrically connected to the heating element, and configured to control the heating element 24 and achieve the each operating temperature. For example, for an embodiment of the gas sensor designed to measure excitation responses of the gas sensing material 22 at a first operating temperature and at a second operating temperature, the heater controller 28 may be configured to provide a first voltage to the heating element 24 to heat the gas sensing element 12 to the first operating temperature when a first set of dielectric excitation responses of the gas sensing material 22 are being measured, and to provide a second voltage to the heating element 24 to heat the gas sensing element 12 to the second operating temperature when a second set of dielectric excitation responses of the gas sensing material 22 are being measured. For example, in certain embodiments, the operating temperatures of the gas sensing material 22 may be between 30° C. and 1000° C., between 50° C. and 900° C., or between 80° C. and 600° C.

For the illustrated embodiment, the sensing electrodes 20 of the gas sensing element 12 are electrically coupled to a measurement circuit 32 of the control circuitry 14 of the gas sensor 10. The measurement circuit 32 is designed to provide at least dielectric excitation to the gas sensing material 22 at preselected frequencies and to measure dielectric responses of the gas sensing material 22 (e.g., impedance responses) to these excitations. In certain embodiments, the measurement circuit 32 may additionally be capable of (or designed to) provide direct current (DC) excitation to the gas sensing material 22 and to measure the DC response (e.g., resistance response) of the gas sensing material 22 to this excitation. In certain embodiments, the measurement circuit 32 may measure both alternating current (AC) and DC responses of the gas sensing material 22. However, in certain embodiments, the measurement circuit 32 may be designed to only provide dielectric excitation to, and only measure dielectric responses of, the gas sensing material 22.

As used herein, "dielectric excitation" of a MOS sensing material refers to an alternating current (AC) excitation of the MOS sensing material at a shoulder of its dielectric relaxation region. As used herein, "impedance" is a non-limiting term for any electrical response of the sensing system to an alternating electrical current applied to the gas sensing material 22. It may be appreciated that such a response may be measured as different electrical properties in different embodiments. Non-limiting examples of these electrical responses of the gas sensing material 22 to alternating electrical current include: impedance, real part of impedance, imaginary part of impedance, admittance, reactance, susceptance, or the like. In the present specification, examples of the responses are given as impedances; however, other electrical responses of the gas sensing material 22 to alternating electrical current excitation may be also equally produced. In one embodiment, the electrical response of the gas sensing material 22 may be monitored at the gas-modulated high-frequency shoulder of the dielectric relaxation region of the sensing material. In one embodiment, the electrical response of the sensing system may be monitored at the gas-modulated low-frequency shoulder of the dielectric relaxation region of the sensing material.

The gas sensor 10 may represent one or more different versions of multi-gas sensing systems described herein. In one or more embodiments, the measurement circuit 32 may include a resistor-capacitor (RC) electrical circuit that includes one or more resistor (R) and capacitor (C) components that may be electronically changed by a controller circuitry 14 by the presence of one or more analyte gases of interest. In one or more embodiments, the measurement circuit 32 may perform dielectric excitation and impedance measurements at one or more different frequencies or at one or more different RC configurations of the measurement circuit 32. For example, the measurement circuit 32 of the gas sensor 10 may measure impedance responses of the gas sensing material 22 at different frequencies, at different resistances of the RC electrical circuit of the measurement circuit 32, at different capacitances of the RC electrical circuit of the measurement circuit 32, or any combination of two or more therein. The measurement circuit 32 provides excitation and measurements of the response of the sensing element to gases. The measurement circuit 32 is not designed to be affected by the measured gas concentrations. Rather, only the gas sensing element 12 is designed to be predictably affected by the measured gas concentrations.

The control circuitry 14 of the illustrated gas sensor 10 includes an on-board data processing unit 34 (also referred to herein as "data processing circuitry" or "data processing unit") that is communicatively coupled to the measurement circuit 32 to receive the excitation responses measured by the measurement circuit 32. The data processing unit 34 includes an on-board, low-power data processor 36 (also referred to herein as simply "data processor"), and includes a memory 38 storing gas analysis models 40, such as gas classification models 42, gas quantitation models 44, or any combination thereof. In certain embodiments, the memory 38 may be integrated into or communicatively coupled with the on-board, low-power data processor 36. The gas analysis models 40 are mathematical models that generally store relationships between excitation responses (e.g., dielectric excitation responses) and particular classifications or concentrations of gases in a fluid sample. For example, the gas classification models 42 may store relationships between excitation responses of the gas sensing material 22 and particular classifications of gases at particular operating temperatures, while the gas quantitation models 44 may store relationships between excitation responses of the gas sensing material 22 and particular concentrations of gases at particular operating temperatures. In certain embodiments, the gas analysis models 40 may include one or more parameters (e.g., coefficients) having values that are calculated from experimentally determined measurements and stored in the memory 38. In some embodiments, the number of analyte gases determined by the gas classification models 42, or gas quantitation models 44, or any combination thereof, for the illustrated gas sensor 10 may range from one analyte gas to fifty analyte gases. The data collected by the gas sensor may be analyzed and processed at the gas sensor 10 instead of sending data wirelessly or by wires to an external computing device. The term "at a sensor" also means on-board, on-chip, or on-edge, where an on-board processor shares any common hardware components with the sensing element, the measurement circuit, and other components of the gas sensor. Non-limiting examples of such hardware components may include a common printed circuit board and a common power source.

A gas sensing element that has two or more responses or outputs is called a multivariable gas sensing element. To analyze outputs from a multivariable gas sensing element, multivariate data processing principles are applied. Multivariate data processing principles can be applied to quantify diversity of responses of a multivariable sensor to different gases. Multivariate transfer functions can be built to quantify different gases. The built multivariate transfer functions can be implemented to quantify different gases in new measurement data from this multivariable gas sensing element. Non-limiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis algorithms include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Non-limiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), or Artificial Neural Network Analysis (ANN). In certain aspects of the inventive subject matter described herein, a classification algorithm can be followed by quantitation algorithm.

For the illustrated embodiment, the gas sensor 10 also includes an ambient environment sensor 17, which may provide ambient environmental data 46 indicative of one or more characteristics of the ambient air 48 in and/or around the gas sensor 10 to the on-board, low-power data processor 36 for storage in the memory 38. The ambient environmental data 46 may include, for example, relative humidity, temperature, atmospheric pressure, wind conditions (e.g., direction, speed, gust), air quality index (AIQ) values, indoor air quality (IAQ) values, particulate pollutants, gaseous pollutants and so forth. For example, the ambient environment sensor 17 may be a capacitive and/or resistive sensor wherein the measured capacitance of the ambient environment sensor 17 corresponds to a relative humidity of the ambient air 48 around the gas sensor 10. For the embodiment illustrated in FIG. 1, the memory 38 of the gas sensor 10 stores ambient environmental data 46 received from the ambient environment sensor 17, such as a temperature, pressure, relative humidity, and so forth, of the ambient air 48.

For the embodiment illustrated in FIG. 1, the memory 38 also stores contextual data 50 received by the on-board, low-power data processor 36 from the one or more input devices 15 of the gas sensor 10. For example, in certain embodiments, the input devices may include one or more communication devices 52 (e.g., a radio-frequency (RF)-based wireless communication device, an infrared (IR)-based wireless communication device) that can communicate with one or more external systems (e.g., an external computing device, an internet-connected server) to retrieve contextual data 50 related to a multi-gas analysis. In certain embodiments, the input devices 15 may include one or more human interface devices 54 (HIDs) (e.g., keyboard, mouse, touchscreen, microphone) that enable contextual data 50 to be received from an operator or user of the gas sensor 10. In certain embodiments, the input devices 15 may include sources of contextual data 50, such as a global positioning system (GPS) device 56 that receives and processes GPS signals to determine a location of the gas sensor 10 for a given multi-gas analysis. The contextual data 50 may be any data related to the conditions of the measurements. For example, for embodiments of the gas sensor 10 used in a medical context, the contextual data 50 received by the one or more input devices 15 may include the age of a patient, the sex of a patient, medical conditions of the patient, the bodily fluid of the patient being analyzed (e.g., blood, sweat, tears, breath), the time and date of the multi-gas analysis, and so forth. In some embodiments, the contextual data 50 may include physical environmental parameters, social parameters, and/or local parameters. A non-limiting list of example of parameters can include schedules of local businesses, municipal waste pickup, information about past or previous events of chemical or other spills or leaks in the area proximate the system, elevated levels of pollutants and/or types of pollutants. In some embodiments, the contextual data 50 includes physiological information regarding a patient associated with the multi-gas analysis, physical environmental information associated with the multi-gas analysis, local event information associated with the multi-gas analysis, or information regarding the deployment of the gas sensor 10 (e.g., an operational age and historical usage of the gas sensor 10, the gas sensing material 22 of the gas sensor 10, how the gas sensor oriented/positioned/worn), or any combination thereof.

While not shown in FIG. 1, in certain embodiments, the control circuitry 14 of the gas sensor 10 may be communicatively coupled to other sensing devices, such as ambient environment sensors 17 that are not integrated into the gas sensor 10 or other gas sensors 10 of a swarm, that may provide additional contextual data 50 to the gas sensor 10 for use in resolving gases in the fluid sample. In certain embodiments, these external sensors may include respective GPS components that provide information regarding the location of each external sensor, such as a distance between the gas sensor 10 and the external sensor (e.g., 0.005 kilometers (km), 0.1 km, 1 km, 10 km). In certain embodiments, a swarm of gas sensors 10 may include a communicatively coupled set of gas sensors 10 including, for example, between 1 and 5 gas sensors, between 5 and 100 gas sensors, between 100 and 1,000 gas sensors, or between 1,000 and 1,000,000,000 gas sensors.

For the embodiment illustrated in FIG. 1, the memory 38 also stores one or more parameter analyzers 58 and a model selector 60. In some embodiments, these components may be implemented as software modules having instructions executable by the on-board, low-power data processor 36. For example, in certain embodiments, each of the one or more parameter analyzers 58 may receive raw data related to a multi-gas analysis (e.g., ambient environmental data 46, contextual data 50, excitation responses of the gas sensing material 22) as inputs, and in response, output analyzed data (e.g., normalized data, filtered data, computed data) based on the received raw data. In certain embodiments, the model selector 60 may receive the analyzed data from each of the one or more parameter analyzers 58 as inputs, and in response, output an indication of which gas analysis models 40 will be used by the on-board, low-power data processor 36 to resolve one or more gases in the fluid sample 26. In some embodiments, the one or more parameter analyzers 58 and the model selector 60 may be combined into a single element that receives raw data related to a multi-gas analysis (e.g., ambient environmental data 46, contextual data 50, excitation responses of the gas sensing material 22) as inputs, and in response, outputs an indication of which gas analysis models 40 will be used by the on-board, low-power data processor 36 to resolve one or more gases in the fluid sample 26. In some embodiments, the one or more parameter analyzers 58 and/or the model selector 60 may be implemented as artificial intelligence agents (e.g., artificial neural networks (ANNs)). For example, one or more ANNs may be trained using human-labeled data sets to associate data related to a multi-gas analysis (e.g., ambient environmental data 46, contextual data 50, excitation responses of the gas sensing material 22) with the desired gas analysis models 40 to be used for resolving the one or more gases in the fluid sample 26.

Accordingly, in certain embodiments, the on-board, low-power data processor 36 uses the one or more parameter analyzers 58 and/or the model selector 60 to processes the ambient environmental data 46, contextual data 50, and/or excitation responses of the gas sensing material 22 to select suitable gas analysis models 40 for resolving the one or more gases in the fluid sample. Additionally, the on-board, low-power data processor 36 selects particular excitation responses (e.g., dielectric excitation responses) for analysis, and provides these excitation responses as inputs to the selected gas analysis models 40, wherein the gas analysis models 40 return outputs that resolve two or more gases in the fluid sample 26. As used herein, "resolving" two or more gases in a fluid sample, or "providing resolution" between two or more gases in a fluid sample, refers determining a respective classification for each of the gases in the fluid sample, determining a respective concentration of the gases in the fluid sample, or determining both respective classifications and respective concentrations of gases in the fluid sample. As used herein, "classifying" or "determining a classification of" an gas refers to determining an exact chemical identity (e.g., ethanol, acetone, hydrogen, carbon monoxide, methane, toluene, benzene) of the gas or determining a chemical class (e.g., a hydrocarbon, an oxide, a sulfide, a ketone, an aromatic hydrocarbon, and so forth) to which each gas belongs.

In certain embodiments, the on-board, low-power data processor 36 is a multicore processor. For example, in some embodiments, the on-board, low-power data processor 36 is a multicore processor on a single integrated circuit with two or more separate processing units (also referred to as cores), each of which reads and executes program instructions. In certain embodiments, the multicore processor may only include a single central processing unit (CPU) and multiple additional cores, while on some embodiments, the multicore processor may include multiple CPUs. For embodiments in which the on-board, low-power data processor 36 is a multicore processor, different gas analysis models and/or different signal processing algorithms may be independently executed by different cores to reduce the power consumption of the data processing unit 34 and/or the gas sensor 10. In one embodiment, the on-board data processing unit 34 can be a microcontroller from Infineon® of the programmable system-on-a-chip (PSoC) 4000 family that has dimensions of 1.45 millimeter (mm)×1.56 mm×0.42 mm. It is appreciated that such an on-board processor microcontroller can easily be placed inside of a 3 mm×3 mm×1 mm package for small form factor applications.

For the illustrated embodiment, the gas sensor 10 includes one or more output devices 16. In certain embodiments, the output devices 16 include one or more display devices 62 that are configured to present information regarding a multi-gas analysis, such as the classification and/or concentration of two or more gases in the fluid sample 26. In some embodiments, other output devices 16 may include alarms 64, such as visual alarms (e.g., light emitting diodes (LEDs)), auditory alarms (e.g., speakers), and/or haptic alarms (e.g., haptic feedback devices). In certain embodiments, the output devices 16 may include one or more communication devices 66 (e.g., wired communication interfaces, RF or IR wireless communication interfaces) that enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in certain embodiments, information determined by the on-board, low-power data processor 36 regarding the resolution of two or more gases in the fluid sample 26 may be provided to an external computing system that serves as a controller of a mesh of sensors that includes the gas sensor 10. In some embodiments, the gas sensor 10 may additionally or alternatively use the communication devices 52, 66 to provide excitation response measurements to an external computing system, such that the external computing system can use these measurements to calculate one or more coefficient values for one or more of the gas analysis models and return these coefficient values to the gas sensor 10 for storage in the memory 38.

Additionally, the illustrated gas sensor 10 includes a battery 68 that is electrically coupled to provide power to various components of the gas sensor 10, including the control circuitry 14 and the output devices 16. It may be appreciated that the battery 68 should have a suitable capacity to power all of the components of the gas sensor 10. For example, this may include: heating the gas sensing material 22, providing dielectric excitation to the gas sensing material 22, measuring the dielectric excitation responses of the gas sensing material 22, analyzing the measured dielectric excitation responses to resolve two or more gases in a fluid sample, and presenting results of the analysis via a suitable output devices 16. In certain embodiments, the battery 68 may has a capacity that is sufficient to operate the gas sensor 10 for at least 10 hours. In some embodiments, the battery 68 may have a battery capacity between 1 milliamp-hour (mAh) and 500 mAh, or between 1 mAh and 200 mAh, or between 1 mAh and 100 mAh. In certain embodiments, such as embodiments in which the gas sensor 10 is designed to be particularly thin (e.g., for ingestible or tattooed embodiments of the gas sensor 10), the battery 68 may have a thickness less than about 5 millimeters (mm). In some embodiments, all of the components of the gas sensor 10 may be coupled to or at least partially disposed within a suitable packaging or housing for a particular gas sensing application. For example, for personal monitoring applications, the packaging of the gas sensor 10 may be made of a biocompatible polymer that can be externally worn, subcutaneously injected, or ingested to perform personal or patient multi-gas analysis. In certain embodiments, the gas sensor 10 may include an energy harvesting module 70 that is electrically coupled to charge the battery 68 using power that is collected from the ambient environment in the form of electromagnetic radiation (e.g., visible light, infrared (IR) light, radio-frequency (RF) waves).

The gas sensor 10 may be in contact with the fluid sample 26 in the form of a fluid vessel that may be a form of a vessel with controlled volume, or in the form of an open area such as an indoor facility (e.g., a room, a hall, a house, a school, a hospital, a confined space, or the like), or in the form of an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, or the like). In one embodiment, the gas sensor 10 may provide continuous monitoring of the fluid sample 26 within the reservoir or flow path. In one or more embodiments, the gas sensor 10 may be an impedance gas sensor, an electromagnetic sensor, an electronic sensor, a hybrid sensor, or another type of sensor. Optionally, the gas sensor 10 may be part of a sensor array.

The fluid sample 26 may be a gas, a liquid, a gas-liquid mixture, a solid, particles or particulate matter, or the like, containing one or more analyte gases therein. In another embodiment, the fluid sample 26 may be a gas or fuel, such as a hydrocarbon-based fuel. One example of the fluid sample 26 is natural gas or hydrogen gas that is supplied to a powered system (e.g., a vehicle, airplane engine, or a stationary generator set) for consumption. Other examples of such a fluid sample 26 can include gasoline, diesel fuel, jet fuel or kerosene, bio-fuels, petrodiesel-biodiesel fuel blends, natural gas (liquid or compressed), and fuel oils. In other embodiments, the fluid sample 26 may be a sample of indoor or outdoor ambient air. For example, the sample may be from an industrial, residential, military, construction, urban, or any other known site. Further, the ambient air sample may include relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical agents such as nerve, blister, blood, and choking agents, hydrocarbons and/or other environmental agents. In other embodiments, the fluid sample 26 may be a disinfecting agent, such as alcohol, aldehyde, chlorine dioxide, hydrogen peroxide, and so forth. In other embodiments, the fluid sample 26 may mix with ambient air 48 from around the gas sensor 10 with relatively small concentrations, medium concentrations, and/or large concentrations of combustible gases such as methane, ethane, propane, butane, hydrogen, and/or other gases. The ambient air 48 may have certain measurable or identifiable characteristics, such as relative humidity, temperature, barometric pressure, concentrations of other gases, etc. In further embodiments, the fluid sample 26 may include at least one gas dissolved in an industrial liquid such as transformer oil, bioprocess media, fermentation media, wastewater, and so forth. The fluid sample 26 may also include at least one gas dissolved in a consumer liquid such as milk, a non-alcoholic beverage, alcoholic beverage, cosmetics, and so forth. In other embodiments, the fluid sample 26 may include at least one gas dissolved in a body liquid such as blood, sweat, tears, saliva, urine, feces, bile, and so forth.

In certain embodiments, the fluid sample 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride. In certain embodiments, the fluid sample 26 may include analyte gases that are toxic materials of the medium Hazard Index. A non-limiting list of example toxic materials of the medium Hazard Index includes, but is not limited to: acetone cyanohydrin, acrolein, acrylonitrile, allyl alcohol, allylamine, allyl chlorocarbonate, boron tribromide, carbon monoxide, carbonyl sulfide, chloroacetone, chloroacetonitrile, chlorosulfonic acid, diketene, 1,2-dimethylhydrazine, ethylene dibromide, hydrogen selenide, methanesulfonyl chloride, methyl bromide, methyl chloroformate, methyl chlorosilane, methyl hydrazine, methyl isocyanate, methyl mercaptan, nitrogen dioxide, phosphine, phosphorus oxychloride, phosphorus pentafluoride, selenium hexafluoride, silicon tetrafluoride, stibine, sulfur trioxide, sulfuryl chloride, sulfuryl fluoride, tellurium hexafluoride, n-octyl mercaptan, titanium tetrachloride, trichloroacetyl chloride, and trifluoroacetyl chloride.

In certain embodiments, the fluid sample 26 may include analyte gases that are toxic materials of the low Hazard Index. A non-limiting list of example toxic materials of the low Hazard Index includes, but is not limited to: allyl isothiocyanate, arsenic trichloride, bromine, bromine chloride, bromine pentafluoride, bromine trifluoride, carbonyl fluoride, chlorine pentafluoride, chlorine trifluoride, chloroacetaldehyde, chloroacetyl chloride, crotonaldehyde, cyanogen chloride, dim ethyl sulfate, diphenylmethane-4,40-diisocyanate, ethyl chloroformate, ethyl chlorothioformate, ethyl phosphonothioic dichloride, ethyl phosphonic dichloride, ethyleneimine, hexachlorocyclopentadiene, hydrogen iodide, iron pentacarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl chloroformate, tert-butyl isocyanate, tetraethyl lead, tetraethyl pyrophosphate, tetramethyl lead, toluene 2,4-diisocyanate, and toluene 2,6-diisocyanate.

In certain embodiments, the fluid sample 26 may include analyte gases that are indoor pollutants. A non-limiting list of example indoor pollutants includes, but is not limited to: acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the fluid sample 26 may include analyte gases that are outdoor pollutants. A non-limiting list of example outdoor pollutants includes, but is not limited to: ozone, nitrogen dioxide, sulfur dioxide, and carbon monoxide.

Embodiments of the gas sensor 10 have the ability to resolve gases at different concentrations in the fluid sample 26. For example, the gas sensor 10 may resolve gases at regulated vapor-exposure limits established by different organizations. In certain embodiments, the gas sensor 10 can resolve analyte gases below a Permissible Exposure Limit (PEL). In some embodiments, the gas sensor 10 can resolve gases below Threshold Limit Value Short-Term Exposure Limit (TLV-STEL). In some embodiments, the gas sensor 10 may resolve analyte gases below Threshold Limit Value Time-Weighted Average (TLV-TWA). In some embodiments, the gas sensor 10 may resolve gases below Immediately Dangerous to Life or Health (IDLH). In certain embodiments, the gas sensor 10 may resolve gases below and above Lower Explosive Limit (LEL). In certain embodiments, the gas sensor 10 may be capable of resolving gases having a concentration less than 5%, less than 100 part-per-million (ppm), less than 100 part-per-billion (ppb), less than 100 part-per-trillion (ppt).

Figure 2A:
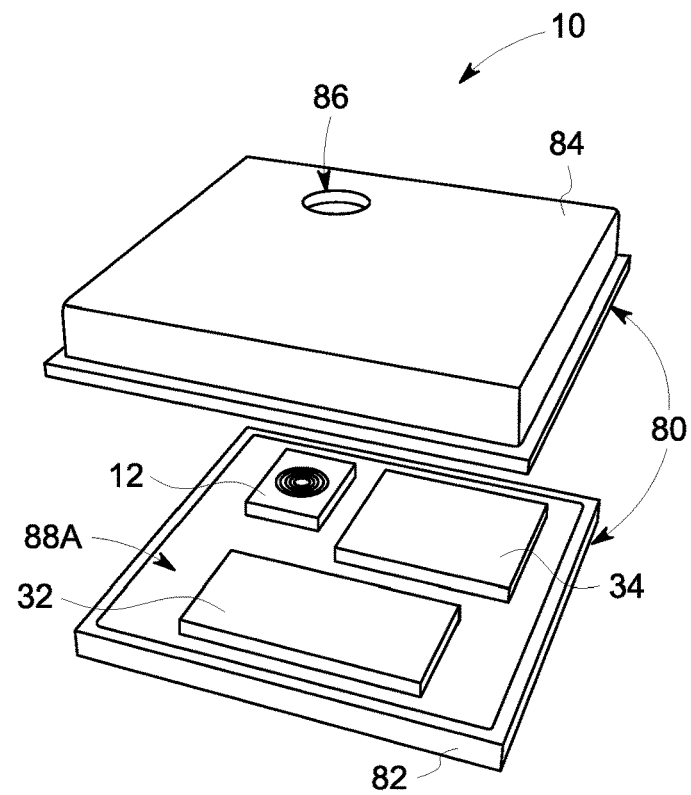
FIGS. 2A and 2B are diagrams of embodiments of the gas sensor for multi-gas analysis of fluid samples, in accordance with aspects of the present technique.
Figure 2B:
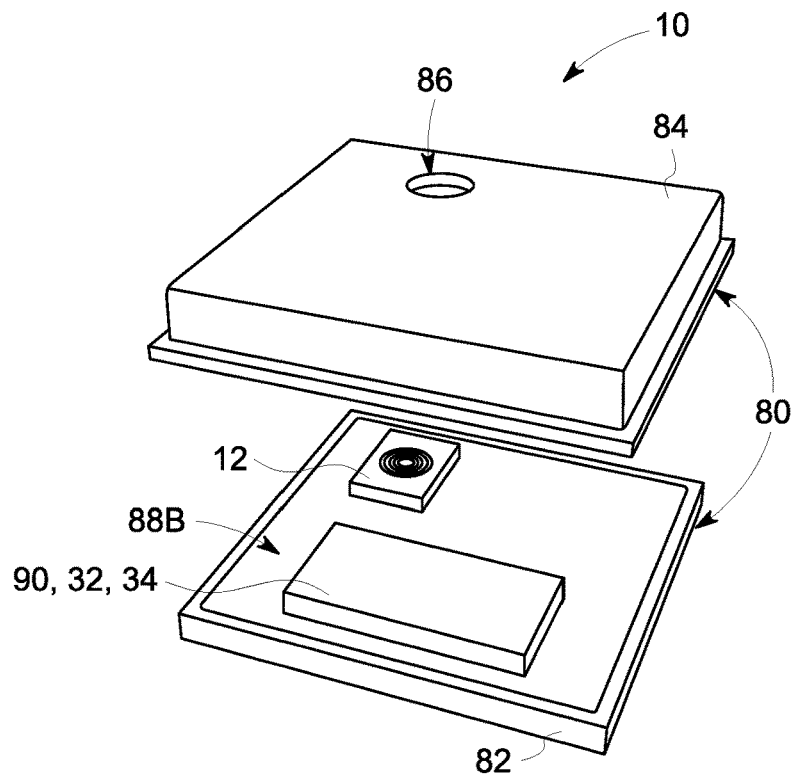

FIGS. 2A and 2B are perspective views of embodiments of the gas sensor 10. In these figures, the gas sensor 10 includes a housing 80 having a base 82 and a lid 84 with an opening 86 below which the gas sensing element 12 is disposed. More specifically, FIG. 2A depicts an embodiment in which the gas sensor 10 includes a micro-package 88A having the gas sensing element 12, the measurement circuit 32 implemented as an application-specific integrated circuit (ASIC), and the separately-implemented data processing unit 34, which is utilized for linear, nonlinear, and non-monotonic multivariate regressions during multi-gas analysis. By comparison, FIG. 2B depicts another embodiment in which the micro-package 88B of the gas sensor 10 includes the gas sensing element 12, while the measurement circuit 32 and the data processing unit 34 are both implemented within a common or shared ASIC 90.

Figure 3A:
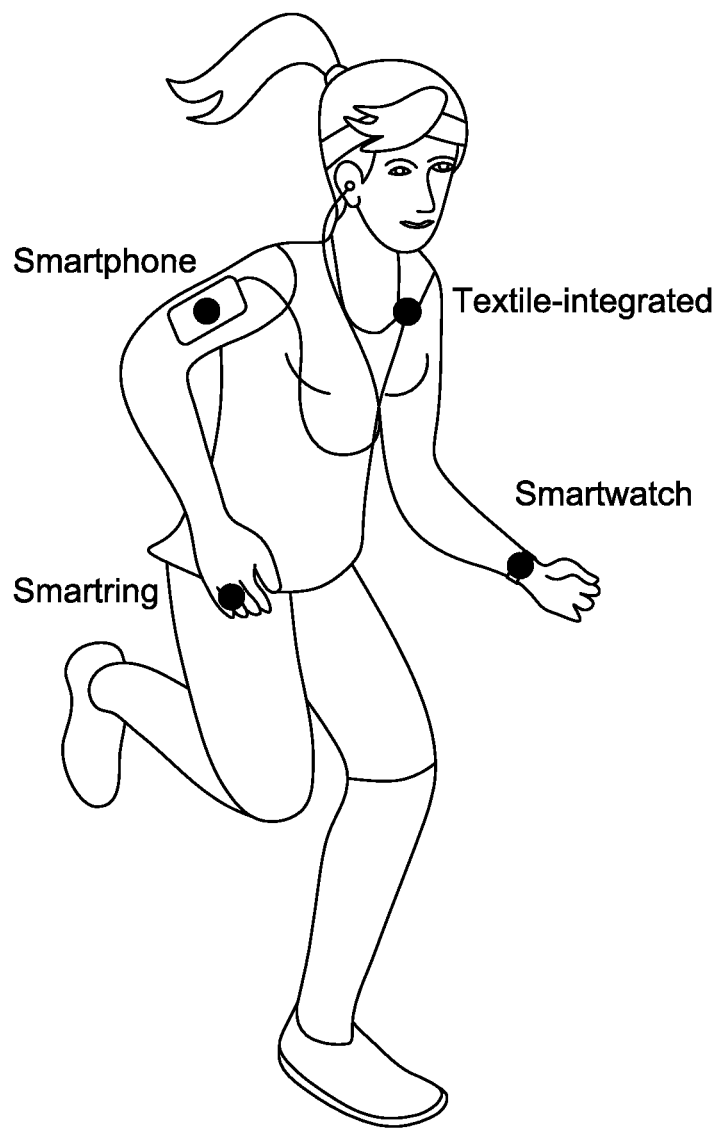
FIGS. 3A and 3B are diagrams illustrating the use of various embodiments of the gas sensor, in accordance with aspects of the present technique.
Figure 3B:
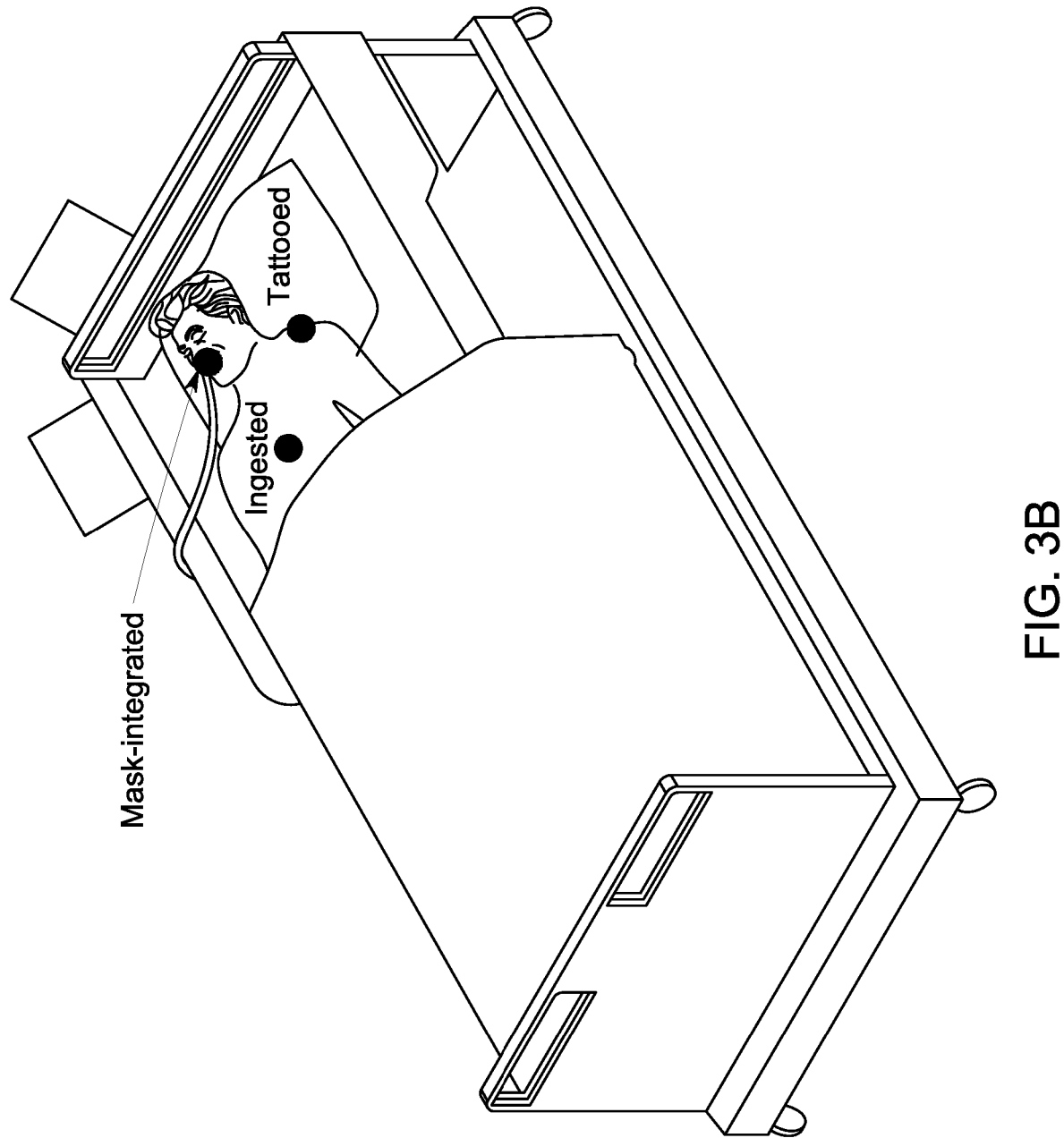

FIGS. 3A and 3B are diagrams illustrating the use of the gas sensor 10 for different applications, such as personal monitoring and patient monitoring. For example, in some embodiments, the gas sensor 10 may be a wearable device that may be worn or moved from one place to another by an operator. The gas sensor 10 may be positioned in or be an integrated part of a helmet, hat, glove, or other clothing attributes. For example, the gas sensor 10 may be held within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a fabric of the clothing, can be positioned on clothing such as on a pocket, can be in a form of an arm band, worn on a wrist or other extremity, or the like. The wearable device may be worn by a subject, such as a human or animal or a robot, may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like. The wearable device may be worn, or otherwise carried, by different subjects or individuals, such as, but not limited to, soldiers, medical professionals, athletes, system operators, students, otherwise active or inactive individuals, or the like. Optionally, the wearable sensing system may be coupled with, integrated with, disposed on, or the like, an asset, such as a moving system such as a drone, a stationary system, or the like. The wearable systems may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like. The wearable device can be fabricated using manufacturing technologies based on complementary metal-oxide-semiconductor electronics, flexible electronics, flexible hybrid electronics and other known approaches to provide conformal and flexible designs, implementations, and use. Optionally, the gas sensor 10 may be a stationary device, may be independently mobile (e.g., detachable from an operator and capable of moving independent of the operator), may be airborne, or the like.

Figure 4:
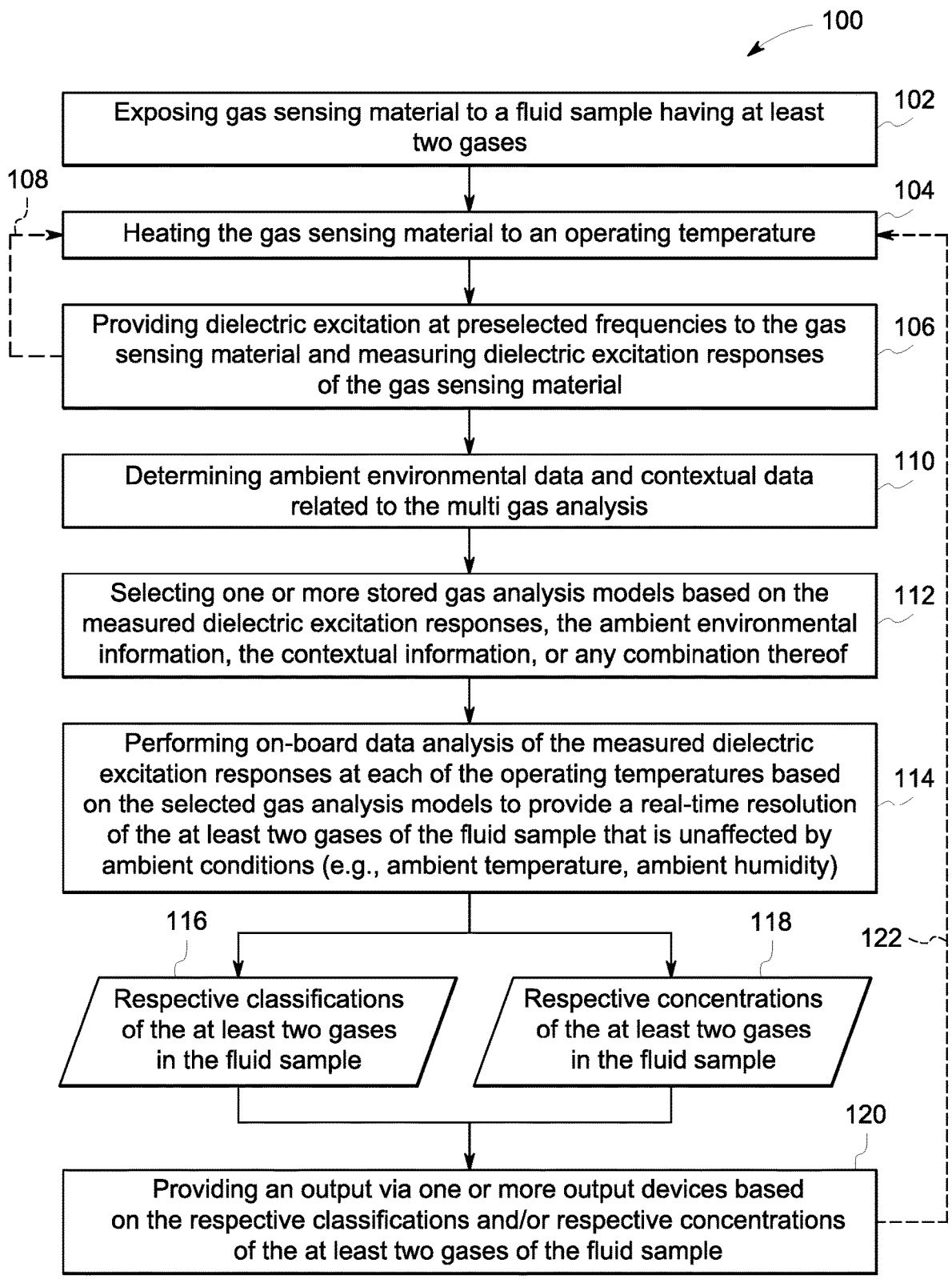
FIG. 4 is a flow diagram illustrating an embodiment of a process whereby the gas sensor performs multi-gas analysis, in accordance with aspects of the present technique.

FIG. 4 is a flow diagram illustrating an embodiment of a process 100 whereby the gas sensor 10 performs multi-gas analysis of a fluid sample 26. The process 100 is discussed with reference to elements illustrated in FIG. 1. For the illustrated embodiment, the process 100 begins with exposing (block 102) the gas sensing material 22 of the gas sensing element 12 to a fluid sample 26 having at least two gases (e.g., at least two analyte gases, at least one analyte gas and one interference gas). For example, the entire gas sensor or only the gas sensing material 22 of the gas sensor 10, may be exposed to the fluid sample 26. The process 100 includes heating (block 104) the gas sensing material 22 to an operating temperature using the heater controller 28 and the heating element 24. Typically, the gas sensing material 22 is heated before, during, and after that it is exposed to the fluid sample 26.

Once the gas sensing material 22 has been exposed to the fluid sample 26 and heated to the first operating temperature, the process 100 proceeds with the measurement circuit 32 providing (block 106) dielectric excitation using at least two preselected frequencies to the gas sensing material 22 operating at the operating temperature, and then measuring dielectric excitation responses (e.g., impedance responses) of the gas sensing material 22. In certain embodiments, the measurement circuit 32 may additionally apply DC excitation to the gas sensing material 22 and measure DC excitation responses (e.g., resistance responses) of the gas sensing material 22 at the operating temperature. However, in some embodiments, the measurement circuit 32 may only measure dielectric excitation responses of the gas sensing material 22 as it contacts the fluid sample 26 at the operating temperature. As indicated by the arrow 108, for embodiments in which excitation responses are collected at multiple operating temperatures, after measuring at least the dielectric responses of the gas sensing material 22 at the first operating temperature, the process 100 may involve returning to block 104 to heat the gas sensing material 22 to a second operating temperature, and again measuring excitation responses (e.g., impedance responses) of the gas sensing material 22 at the second operating temperature in block 106. It may be noted that, in some embodiments, such as a multi-gas analysis involving three or more gases, the process 100 may include any suitable number of addition steps in which the gas sensing material 22 is heated to another (e.g., a third, a fourth, a fifth, etc.) operating temperature, while the measurement circuit 32 measures at least the dielectric excitation responses of the gas sensing material 22, as generally indicated by the arrow 108 in FIG. 4.

Traditionally, MOS gas sensors 10 measure a DC resistance response of a MOS-based sensing element 12 and relate the measured DC resistance response to a concentration of a gas using a power-law relation between the measured resistance and gas concentration. Such DC resistance responses from a MOS gas sensor 10 may be provided as a signal output (e.g., to a user) in a form of an analog signal. Depending on the design of an analog circuit, an analog signal from a MOS gas sensor 10 may represent linear resistance, logarithmic resistance, or conductivity. Alternatively DC resistance responses from a traditional MOS-based gas sensor 10 may be provided as a signal output in a form of a digitized DC resistance response signal. Dependent upon the design of an analog/digital circuit, the digital signal from a MOS gas sensor 10 may be correlated with linear resistance, logarithmic resistance, or conductivity. A digital signal from a MOS gas sensor 10 that is correlated with its DC resistance response can be provided (e.g., to the user) by any of digital communication protocols, for example an I2C (Inter-Integrated Circuit), alternatively known as IIC, and any other communication protocols.

For the illustrated embodiment, the process 100 continues with the on-board, low-power data processor 36 determining (block 110) ambient environmental data 46 and/or contextual data 50 related to the multi-gas analysis. As discussed above, the on-board, low-power data processor 36 may receive ambient environmental data 46 collected by the ambient environment sensor 17, contextual data 50 collected by the one or more input devices 15, and/or excitation responses measured by the measurement circuit 32, and may provide at least a portion of this data as inputs to one or more parameter analyzers 58 and/or the model selector 60 for the selection of the gas analysis models 40. In response, the one or more parameter analyzers 58, the model selector 60, or a combination thereof, provide an output indicating which of the stored gas analysis models 40 should be used to resolve the gases in the fluid sample 26, and based on this output, the on-board, low-power data processor 36 selects (block 112) the one or more stored gas analysis models 40.

For the illustrated embodiment, the process 100 continues with the on-board, low-power data processor 36 of the gas sensor 10 performing (block 114) on-board data analysis of the measured dielectric excitation responses at each of the operating temperatures based on the selected stored gas analysis models 40 to provide a real-time resolution of the gases in the fluid sample that is unaffected by ambient conditions (e.g., ambient temperature, ambient humidity). For example, the on-board, low-power data processor 36 may determine respective classifications 116 of each of the at least two gases in the fluid sample 26, respective concentrations 118 of each the at least two gases in the fluid sample 26, or a combination thereof. For certain embodiments in which the DC excitation response is also measured by the measurement circuit 32, the on-board, low-power data processor 36 may also provide the DC excitation response as inputs to at least one of the stored gas analysis models 40 when resolving the gases in the fluid sample. In this context, "real-time" refers to the on-board, low-power data processor 36 of the gas sensor 10 being able to locally, rapidly resolve gases in the fluid sample without requiring the measured excitation responses be provided to an external computing system for processing.

For the embodiment of the process 100 illustrated in FIG. 4, after resolving the gases in the fluid sample 26, the gas sensor 10 may use one or more output devices 16 to provide an output (block 120) the respective classifications 116 of the gases in the fluid sample 26, the respective concentrations 118 of the gases in the fluid sample 26, or both. For example, one or more output devices 16 of the gas sensor 10 may present or display the respective classifications 116 and/or the respective concentrations 118 of the gases in the fluid sample 26. In certain embodiments, the gas sensor 10 may provide the respective classifications 116 and/or the respective concentrations 118 of the gases to an external computing system via one or more suitable communication devices 66 (e.g., a wireless communication interface) of the gas sensor 10. In certain embodiments, the gas sensor 10 may use one or more output devices 16 to output the respective alarms 64 of the presence of gases in the fluid sample above certain predetermined threshold levels stored in the memory 38 of the gas sensor 10. Additionally, in certain embodiments, the process 100 may proceed by returning to block 104 and repeating the remaining steps of the process 100 for a predetermined length of time or until a predetermined number of cycles, as indicated by the arrow 122.

Figure 5:
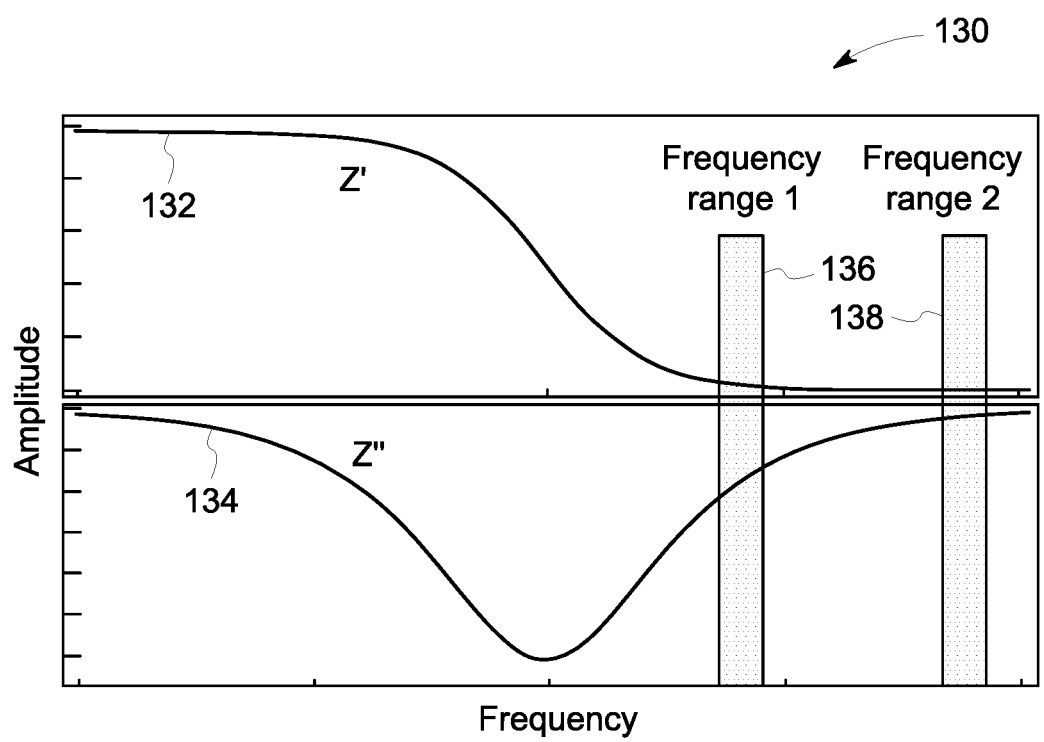
FIG. 5 is a graph of an example impedance spectrum of a gas sensing material of the gas sensor of FIG. 1 with preselected frequencies for dielectric excitation, in accordance with aspects of the present technique.

FIG. 5 is a graph illustrating an example impedance spectrum 130. In impedance spectroscopy, measurements of the real part Z' and the imaginary part Z" of the impedance may be performed over a broad range of frequencies to determine the shape of the impedance spectrum 130 of the gas sensor 10. As illustrated, the impedance spectrum includes two curves, each representing part of the impedance response of the gas sensor 10 over a broad range of frequencies to determine the shape of the impedance spectrum. In particular, a first curve 132 represents the real part (Z') of the impedance of gas sensor 10, while a second curve 134 represents the imaginary part (Z") of the impedance of the gas sensor 10 as measured over a broad range of frequencies. Unlike broad-band impedance spectroscopy measurements, the dielectric excitation measurements are performed over specific frequency ranges by following the front (high- or low-frequency) shoulder of the dielectric relaxation region obtained from impedance measurements of (n- or p-type, respectively) MOS materials when they are exposed to various gas concentrations.

For present embodiments, the measurement circuit 32 is or includes an impedance detector that measures the dielectric excitation response of the gas sensor 10 at two or more frequency ranges 136, 138 (which may or may not be disposed in the "dielectric relaxation region" of the gas sensor 10). For example, in certain embodiments, each dielectric excitation response measured by the measurement circuit 32 may include a combination (e.g., a sum, a difference, any other mathematical representation) of a value from the first curve 132 (e.g., a real impedance value) and a value from the second curve 134 (e.g., an imaginary impedance value), both selected from the frequency ranges 136, 138. Alternatively, in some embodiments, each dielectric excitation response measured by the measurement circuit 32 may include a combination (e.g., a sum, a difference, any other mathematical representation) of a value from the first curve 132 (e.g., a real impedance value Z') and a value from the second curve 134 (e.g., an imaginary impedance value Z"), both selected from the frequency ranges 136, 138, or other frequency ranges. Selection of the frequency ranges 136, 138 may depend on type of the gas sensing element 12 of the gas sensor 10. For example, related to the gas sensing element 12, the selection of the frequency ranges 136, 138 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected for measurements. For example, response at the frequency ranges 136, 138 may include data indicative of sensor response to gases in the fluid sample. The identities and/or concentrations of gases in the fluid sample may then be determined based on the sensor response at the first and second frequency ranges 136, 138.

An assessment was performed involving applying various data processing algorithms to build gas analysis models 40 to predict concentrations of gases and applying these models using the on-board, low-power data processor 36 of the gas sensor 10 to perform multi-gas analysis. Table 1 includes a non-limiting list of four example data processing algorithms, and indicates the resource usage for each of the algorithms for on-board analysis by the gas sensor 10, as well as the resource usage to implement trained models. It is presently recognized that, while building a gas analysis model (e.g., determining the relevant parameters or coefficients of the model) involves substantial data processing, once the model has been constructed and/or trained, the processor usage of the on-board, low-power data processor 36 to subsequently utilize this model to perform on-board, real-time resolution of the gases in the fluid sample 26 is substantially lower. In Table 1, the first column includes the names of the four example machine learning algorithms that could be utilized for multi-gas analysis. It is presently recognized that the indicated algorithms generally demonstrate desired diverse applicability and robustness. The second column of Table 1 indicates the general relations for the number of floating-point operations involved for each type of model based on the number of measurement inputs ($N_{imp}$), as well as other model-specific parameters, such as the number of support vectors ($N_{vec}$), the number of decision trees ($N_{tree}$), the number of nodes in a single hidden layer of the neural net ($N_{node}$), and the number of output nodes in the neural net ($N_{out}$). For this assessment, a value of 20 was used for the number of measurement inputs, which includes, at most, four independent dielectric frequencies to be used for measurement, wherein, for each dielectric frequency, there are two independent temperatures/sensors with a real and imaginary response. For the other model-specific parameters, largest values for typical use cases were assumed (e.g., $N_{vec}=20$, $N_{tree}=20$, $N_{node}=100$, $N_{out}=100$). The third column of Table 1 indicates the order of magnitude for the number of floating-point operations that would be involved for the on-board, low-power data processor 36 to analyze a single excitation measurement. In addition to the processor usage, each machine learning model stores model parameters in the memory 38 of the gas sensor 10, and the fourth column of Table 1 indicates the amount of space (in kilobytes (kB)) in the memory 38 that is utilized for each model type.

TABLE 1

| Machine Learning Algorithm/Model | Formula for Floating Point Operations for One measurement | Number of Floating Point Operations Per Measurement | Memory Usage |
|---|---|---|---|
| Linear Regression | $N_{inp}$ | ~100 | ~0.5 kB |
| Support Vector Machine | $N_{vec} N_{inp}$ | ~1,000 | ~2 kB |
| Decision Tree | $N_{tree} N_{inp}$ | ~1,000 | ~10 kB |
| Artificial Neural Network | $N_{inp} N_{node} + N_{node} N_{out}$ | ~10,000 | ~40 kB |

In an embodiment, the data processing unit 34 may be an ARM® Cortex® M4F having an on-board, low-power data processor 36 running at a frequency of 64 megahertz (MHz). This on-board, low-power data processor 36 can perform approximately $10^7$ floating-point operations per second. Comparing the processor specifications to values in Column 3 of Table 1 demonstrates that, for all models, a measurement data set of 20 inputs will be able to be processed into an output value in substantially less than one second. Therefore, it is presently recognized that, no matter which of the example models is used, the speed of this example on-board, low-power data processor 36 will not be a limiting factor for the response rate of the gas sensor 10. In certain embodiments, the memory 38 of the data processing unit 34 includes 512 kB of available nonvolatile flash memory. For such embodiments, it is estimated that around half of the available memory will be utilized to hold the software acting as the operating system of the gas sensor 10. Accordingly, for such embodiments, approximately 200 kB of the memory 38 remains available to store parameters of the gas analysis models 40, and this amount is well-above the memory usage listed for each of the example models, as indicated in Column 4 of Table 1.

In certain embodiments, for initial training or recalibration of the gas analysis models 40 of the gas sensor 10, the gas sensor 10 may be communicatively coupled to an external computing system (e.g., desktop computer, laptop computer, an internet-connected server), and may provide the multivariate raw data collected by the gas sensor to the external computing system, such that the external computing system can determine new or updated calibration coefficients for a multivariate transfer function. Subsequently, the new or updated multivariate calibration coefficients may be transferred to the gas sensor 10 and stored within the memory 38 as part of the gas analysis models such that the gas sensor 10 can subsequently utilize the updated gas analysis models 40 when resolving the gases in the fluid sample 26.

However, in certain embodiments, the coefficients of the gas analysis models 40 may be advantageously determined or updated by the on-board, low-power data processor 36 without the use of an external computing device, which reduces the cost and complexity of the system. For example, in such embodiments, the on-board, low-power data processor 36 collects the multivariate raw data from the excitation responses of the gas sensing material 22 and, using this raw data, the on-board, low-power data processor 36 updates the multivariate calibration coefficients and/or the on-board multivariate transfer function of the gas analysis models 40. It may be appreciated that this approach enables the seamless refreshment of gas sensors 10 deployed in the field. For example, if for multivariate analysis operation a certain amount of processing power is utilized (e.g. 1× power), then approximately ten to one hundred times (e.g., 10×-100×) more processing power is utilized for initial training or calibration of the gas analysis models 40. In some cases, such as when the support vector machine (SVM) listed in Table 1 is used, approximately 4,000 iterations are performed to converge to the best transfer function coefficients, wherein the number of iterations is proportional to the number of floating point operations per measurement (e.g., column 3 of Table 1).

It is presently recognized that, to have thousands of iterations to converge to an updated set of calibration coefficients using the on-board, low-power processor 36, the on-board, low-power processor 36 may spend approximately 10× to 1000× more time, as well as substantially more power from the battery 68 and space within the memory 38, to perform these calculations, as compared to operation of the gas sensor 10 when performing multi-gas analysis once the gas analysis models 40 have been determined and/or updated. Additionally, it is recognized that certain data processors have sufficient speed and memory to effectively converge to the updated set of calibration coefficients without extended delay; however, some of these data processors may be too large (e.g., bigger than 3 mm×3 mm×1 mm) for certain embodiments in which the gas sensor 10 desirably has a small form factor.

With this in mind, in certain small form factor embodiments, the respective data processing units 34 of a set of gas sensors 10 (e.g., deployed as part of a gas sensor system or mesh) can be utilized to perform a swarm computing activity to update on-board multivariate calibration coefficients and/or to update an on-board multivariate transfer function for the gas analysis models 40 of a particular deployed gas sensor 10. For example, in such embodiments, this swarm computing can be performed during downtime of the gas sensor system, for example, during night-time when the gas sensing system is not being used for its intended gas-sensing application, enabling the gas sensor 10 to be recalibrated in the field. For such embodiments, processor and memory usage can be distributed across other gas sensors 10 of the gas sensing system, such that computations can be distributed across the on-board, low-power data processors 36 and the memories 38 of the gas sensors 10 of the system. In one embodiment, collecting training and calibration data from neighbor gas sensor 10 located in similar environments can also provide distributed training that can lead to more robust gas analysis models 40. For use cases that involve additional memory and/or processing resources, three-dimensional (3D) device integration techniques (e.g. wire bonding, flip chip) can be utilized to minimize device dimension by creating a vertical stack of these larger devices as a 3D system in package (SiP).

EXPERIMENTAL EXAMPLE

To further demonstrate the superior performance of the disclosed technique, different data analysis techniques from gas-sensing experiments were compared using an embodiment of the gas sensor 10 in which the data processing unit 34 is a microcontroller board Arduino® Mega 2560, which is based on ATmega2560 microcontroller. This example data processing unit 34 includes 256 kB of memory 38 (e.g., flash program memory). For embodiment in which the operating system of the gas sensor 10 consumes approximately half of the memory 38, approximately 128 kB of the memory 38 is available to store model parameters (e.g., coefficients) of the gas analysis models 40. The speed or frequency of the on-board, low-power data processor 36 of this example data processing unit 34 is 16 MHz (MIPS). A measured average for floating-point operations using this example data processing unit 34 takes approximately 5000 ns, which results in approximately 200,000 floating-point operations per second. For this experiment, gas sensing was performed using a $SnO_2$ metal oxide gas sensing material 22 doped with a metal salt, and the measurement circuit 32 of the gas sensor 10 was configured to measure dielectric excitation responses of the gas sensing material 22. Multi-gas analysis was performed using two operating temperatures of approximately 250° C. and approximately 350° C., corresponding to heating element voltages of 1.6 V and 2.4 V, and using two gases, carbon monoxide (CO) and methane ($CH_4$), at several concentrations. For this experiment, the six CO concentrations were 294.12 ppm, 588.24 ppm, 882.35 ppm, 1176.5 ppm, 1470.6 ppm, and 1764.7 ppm; and the five $CH_4$ concentrations were 1.1765 percent by volume (% vol), 2.3529% vol, 3.5294% vol, 4.7059% vol, and 5.8823% vol. The accuracy of predicted concentrations of CO and $CH_4$ gases was compared using the polynomial and support vector machine (SVM) algorithms.

Figure 6:
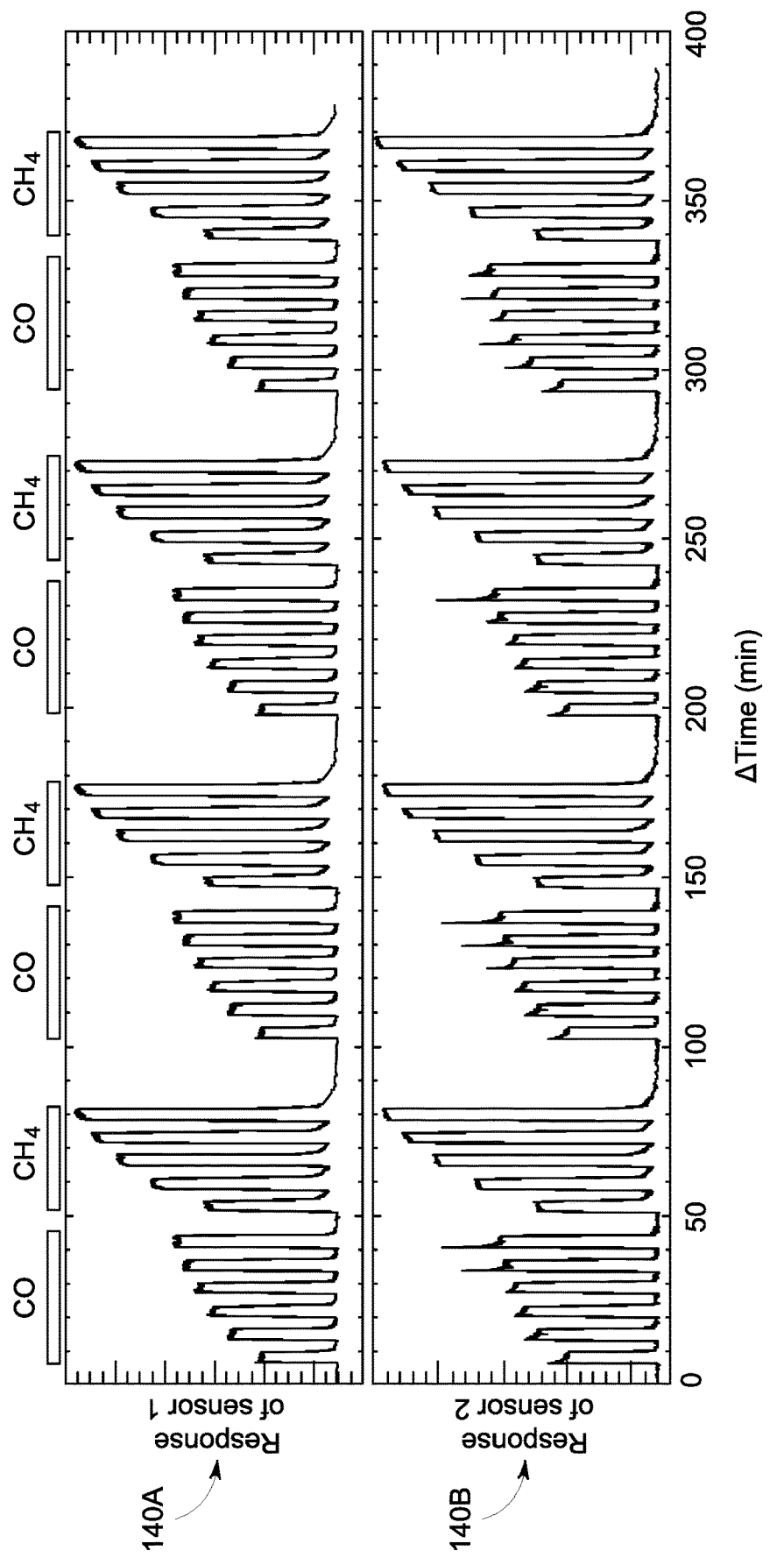
FIG. 6 is a set of graphs illustrating four replicates of dielectric excitation responses of the gas sensor to different concentrations of two gases at two different operating temperatures in an experimental example, in accordance with aspects of the present technique.
Figure 7:
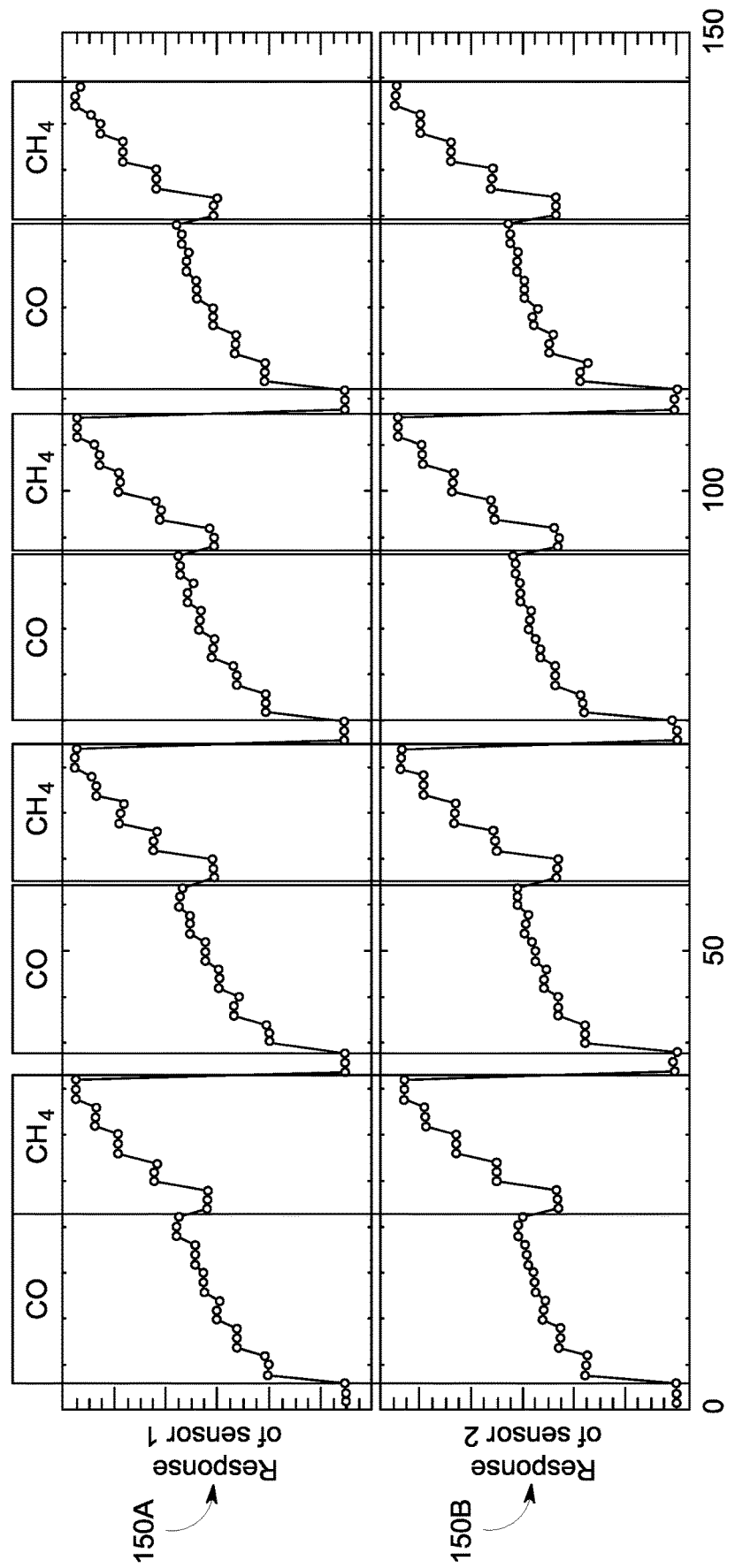
FIG. 7 is a set of graphs illustrating data points extracted at each concentration of the two gases from the graphs of FIG. 6 for the experimental example, in accordance with aspects of the present technique.
Figure 8:
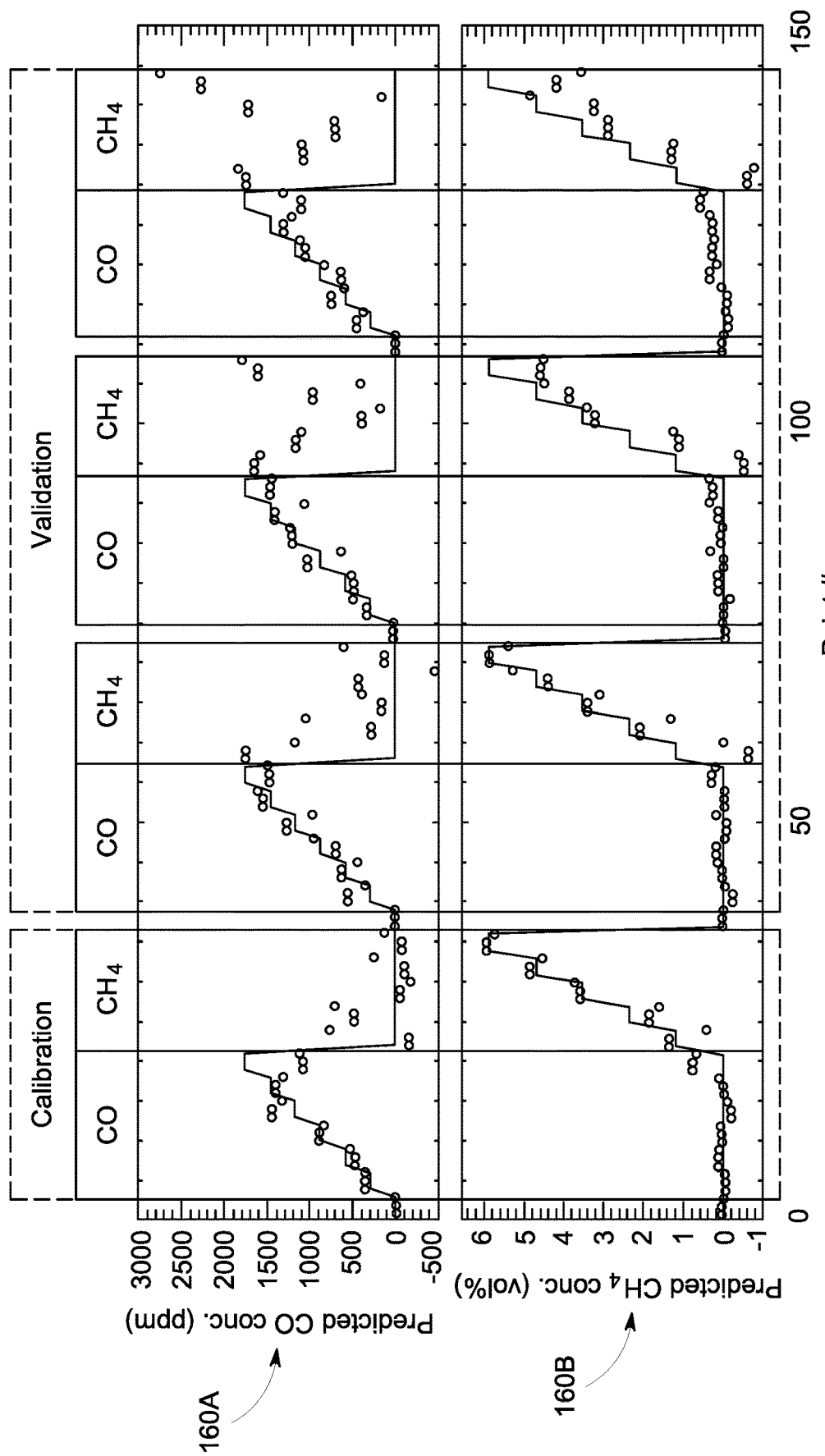
FIG. 8 is a set of graphs illustrating calibration and prediction results for the concentrations of the two gases of the experimental example using a developed third order polynomial model, in accordance with aspects of the present technique.

Four replicates of dielectric excitation responses of the gas sensing material 22 to CO and $CH_4$ at operation voltages of 1.6 V and 2.4 V are depicted by the plots 140A and 140B of FIG. 6. For the data analysis, three data points were extracted from the dielectric excitation responses of the gas sensing material 22 at each of concentrations of the two gases, as depicted by the plots 150A and 150B of FIG. 7. Calibration and prediction results were obtained using the first replicate of the response for calibration and the last three replicates for validation. Calibration and prediction results of concentrations of CO and $CH_4$ gases using developed third order polynomial models are presented in plots 160A and 160B of FIG. 8, respectively. These results demonstrate the quality of the quantitation of concentrations of CO and $CH_4$ gases over the four replicates of the collected raw data.

Figure 9:
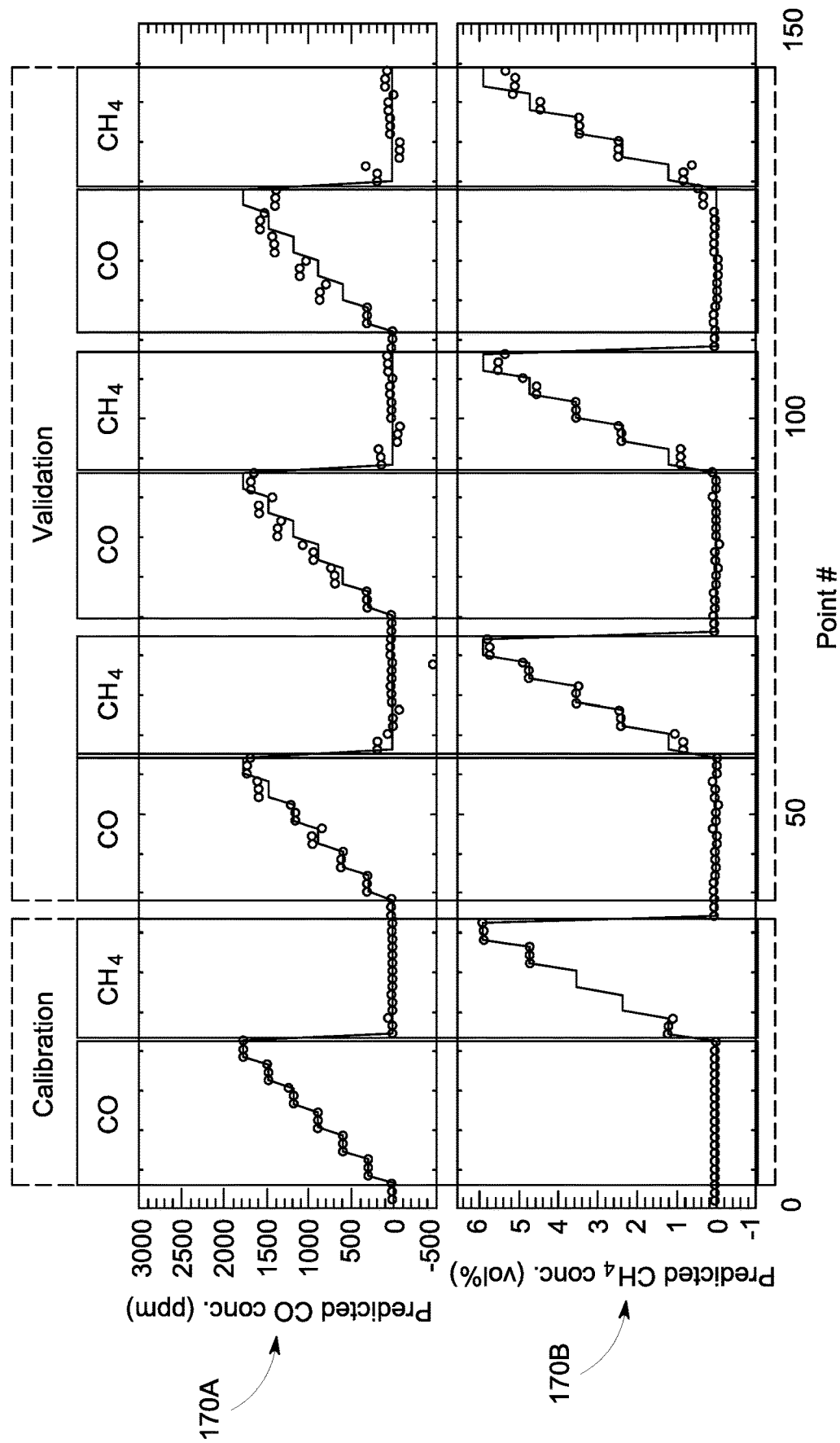
FIG. 9 is a set of graphs illustrating calibration and prediction results of concentrations of the two gases of the experimental example using developed support vector machine (SVM) models, in accordance with aspects of the present technique.
Figure 10A:
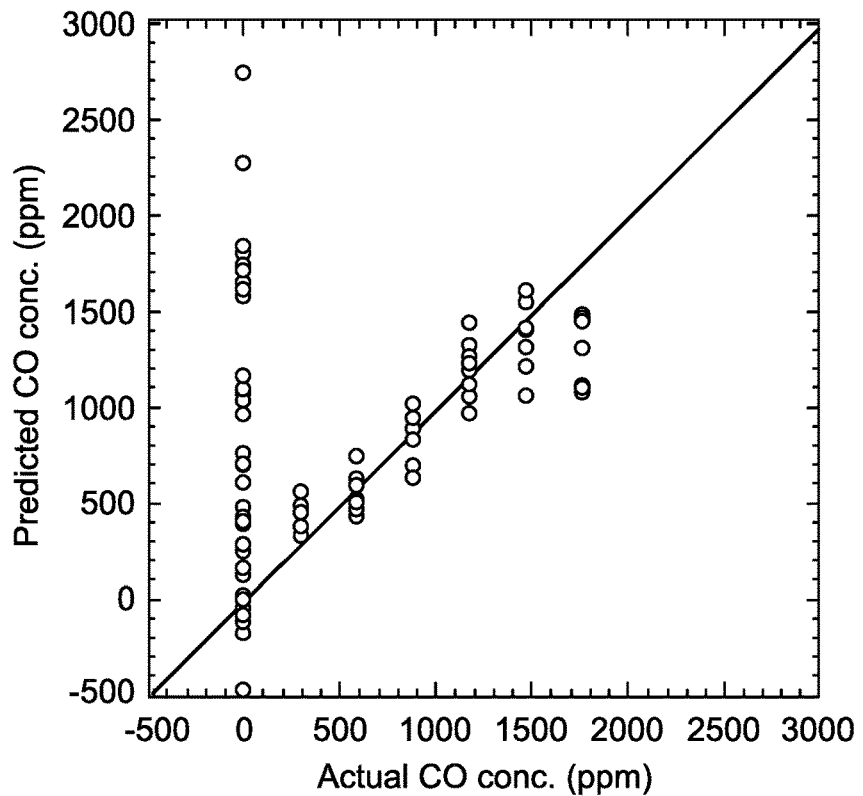
FIGS. 10A and 10B are graphs illustrating correlation plots of the actual and predicted concentrations of the two gases of the experimental example using a third order polynomial for all four replicates, in accordance with aspects of the present technique.
Figure 10B:
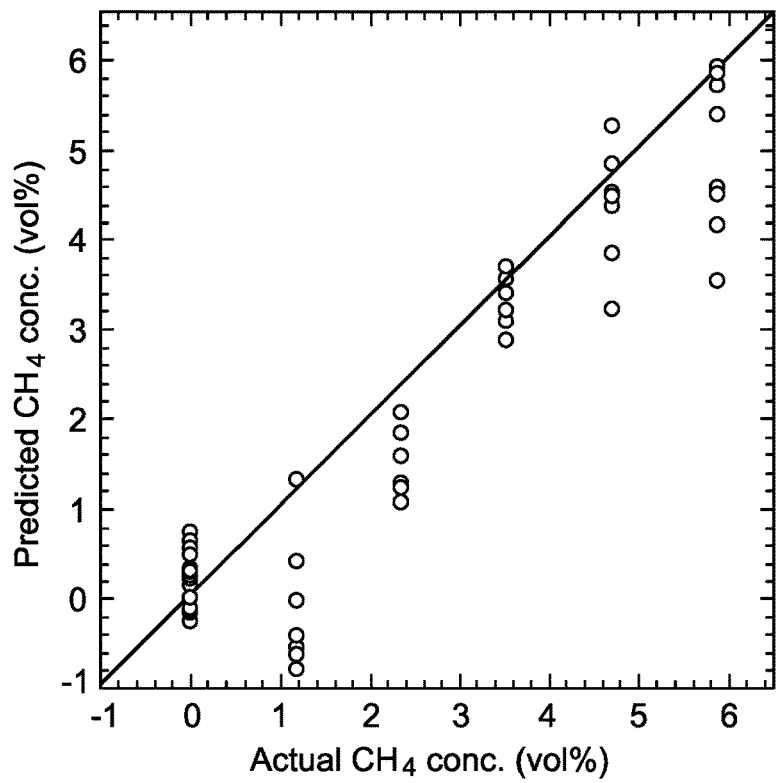
Figure 11A:
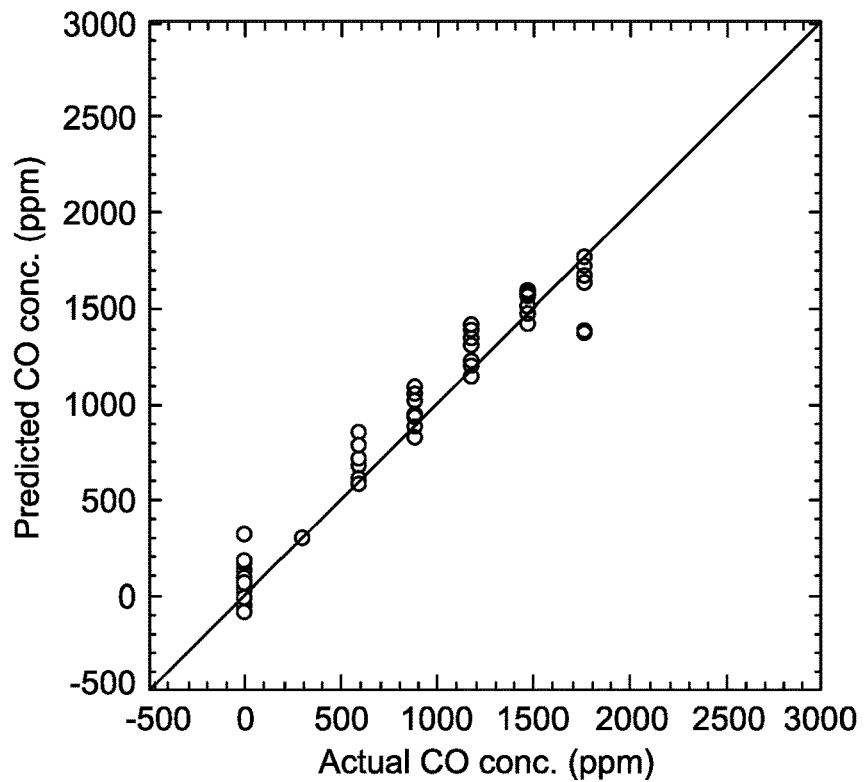
FIGS. 11A and 11B are graphs illustrating correlation plots of the actual and predicted concentrations of the two gases of the experimental example using the developed SVM models for all four replicates, in accordance with aspects of the present technique.
Figure 11B:
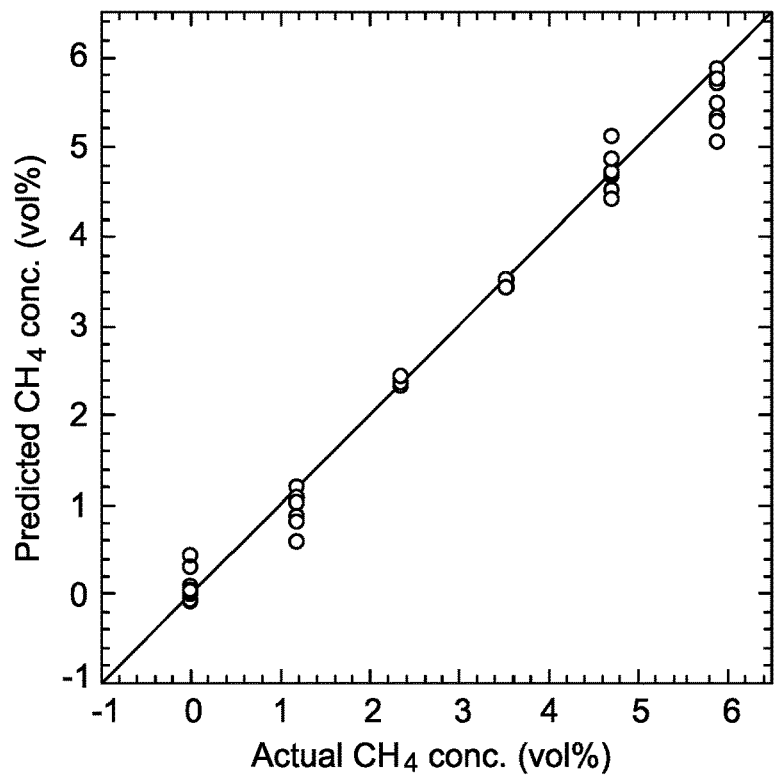

Calibration and prediction results of concentrations of CO and $CH_4$ gases using the developed SVM models are presented in plots 170A and 170B of FIG. 9, respectively. These results demonstrate the improved quality of the quantitation of concentrations of CO and $CH_4$ gases over the four replicates of the collected raw data, as compared to the results using the third order polynomial models. Correlation plots of the actual and predicted concentrations of CO and $CH_4$ using a third order polynomial for all four replicates are illustrated in FIGS. 10A and 10B, respectively. Correlation plots of the actual and predicted concentrations of CO and $CH_4$ using the developed SVM models for all four replicates are presented in FIGS. 11A and 11B, respectively. These results demonstrate that the quality of the quantitation of concentrations of CO and $CH_4$ gases over the four replicates of the collected raw data using SVM was superior than the results obtained using the third order polynomial.

Technical effects of the invention include gas sensor having an on-board, low-power, data processor that uses multivariable gas classification and/or gas quantitation models to perform on-board data processing to resolve two or more gases in a fluid sample. It is presently recognized that data processors for multivariate analysis of multi-gas-sensing data have a significant trade-off between a desired high performance (e.g., a desired accuracy of predicted gas classifications and concentrations) and a desire to minimize power consumption for the data processing that determines the predicted gas classifications and concentration. As such, present embodiments are directed to gas sensors that provide a technical solution for achieving a desired accuracy of predicted gas classifications and concentrations, while minimizing power consumption of the data processor when determining these predicted gas classifications and concentrations. To reduce the computational complexity (and thus the power consumption of the data processor), present embodiments utilize relatively low-power-consumption multivariable data analysis algorithms, inputs from available on-board sensors of ambient conditions (e.g. ambient temperature, humidity, pressure), and/or inputs representing contextual data (e.g. location, surroundings). Based on these inputs, the on-board, low-power data processor of the gas sensor selects suitable gas classification and/or gas quantitation models from a stored library of models, which are generally less complex than corresponding global comprehensive models. The data processor can then utilize these gas classification and quantitation models, in combination with measured dielectric responses of a gas sensing material of the gas sensor, to determine classifications and/or concentrations of two or more gases in a fluid sample, while consuming substantially less power than would be consumed if a global comprehensive model were used instead. Thus, the data processor is utilized for linear, nonlinear, and non-monotonic multivariate regressions. In some embodiments, the power consumed by the data processor when resolving gases in the fluid sample is less that the power that would be consumed for the gas sensor to power a radio-frequency (RF) communication device (e.g., to provide the measurements to an external computing system for data processing).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gas sensor for multi-gas analysis of a fluid sample, comprising:
   a gas sensing element configured to contact the fluid sample;
   a measurement circuit operatively coupled to the gas sensing element and configured to provide dielectric excitation to, and to measure dielectric excitation responses of, the gas sensing element while the gas sensing element contacts the fluid sample; and
   a data processing unit communicatively coupled to the measurement circuit, wherein the data processing unit comprises a memory storing gas analysis models and an on-board, low-power data processor configured to resolve at least two gases of the fluid sample by:
     receiving, from the measurement circuit, the dielectric excitation responses of the gas sensing element while the gas sensing element contacts the fluid sample;
     determining contextual data associated with the multi-gas analysis of the fluid sample;
     selecting, from the memory, at least one of the gas analysis models stored in the memory based, at least in part, on the received dielectric excitation responses of the gas sensing element, the determined contextual data, or any combination thereof;
     selecting and providing, as inputs to the at least one selected gas analysis model, at least a portion of the received dielectric excitation responses to determine outputs of the at least one selected gas analysis model; and
     determining a respective classification, or a respective concentration, or a combination thereof, for the at least two gases in the fluid sample based on the outputs of the at least one selected gas analysis model.

2. The gas sensor of claim 1, wherein the gas sensor comprises at least one ambient environment sensor communicatively coupled to the data processing unit and configured to collect ambient environmental data of an ambient environment associated with the multi-gas analysis, and wherein the on-board, low-power data processor is configured to resolve the at least two gases in the fluid sample by:
   receiving, from the at least one ambient environment sensor, the ambient environmental data, wherein the on-board, low-power data processor is configured to select the at least one gas analysis models based, at least in part, on the received ambient environmental data.

3. The gas sensor of claim 2, wherein the ambient environmental data comprises a relative humidity of the ambient environment, a temperature of the ambient environment, an atmospheric pressure of the ambient environment, wind conditions of the ambient environment, an air quality index (AIQ) of the ambient environment, or an indoor air quality (IAQ) of the ambient environment, or any combination thereof.

4. The gas sensor of claim 1, wherein the contextual data comprises physiological information regarding a person associated with the multi-gas analysis, physical environmental information associated with the multi-gas analysis, local event information associated with the multi-gas analysis, or an operational age of the gas sensor, or any combination thereof.

5. The gas sensor of claim 1, wherein the gas analysis models comprise one or more analyte gas classification models, one or more analyte gas quantitation models, or any combination thereof.

6. The gas sensor of claim 1, wherein the gas analysis models comprise a linear multivariate regression model, a non-linear multivariate regression model, or a non-monotonic multivariate regression model, or any combination thereof.

7. The gas sensor of claim 1, wherein the gas analysis models comprise a support vector machine (SVM) model, a decision tree model, or an artificial neural network (ANN) model, or any combination thereof.

8. The gas sensor of claim 1, wherein the gas sensor is a wearable gas sensor, an ingestible gas sensor, or a tattooed gas sensor.

9. The gas sensor of claim 1, wherein the gas sensor is industrial environmental sensor, an asset monitoring sensor, an industrial process monitoring gas sensor, a consumer sensor, a transportation sensor, a homeland security sensor.

10. The gas sensor of claim 1, wherein, after resolving the at least two gases in the fluid sample, the on-board, low-power data processor is configured recalibrate the gas sensor by recalculating one or more new coefficient values of the gas analysis models stored in the memory based on the received dielectric excitation responses.

11. The gas sensor of claim 1, wherein, after resolving the at least two gases in the fluid sample, the on-board, low-power data processor is configured recalibrate the gas sensor by:
providing the received dielectric excitation responses to an external computing system;
receiving, from the external computing system, one or more recalculated coefficient values of the gas analysis models stored in the memory; and
storing the one or more recalculated coefficient values to update the gas analysis models stored in the memory.

12. The gas sensor of claim 1, wherein, after resolving the at least two gases in the fluid sample, the on-board, low-power data processor is configured recalibrate the gas sensor by:
providing the received dielectric excitation responses to one or more other sensors of a swarm of communicatively coupled sensors;
receiving, from the one or more other sensors, one or more recalculated coefficient values of the gas analysis models stored in the memory; and
storing the one or more recalculated coefficient values to update the gas analysis models stored in the memory.

13. A method of operating an on-board, low-power data processor of a gas sensor for multi-gas analysis of a fluid sample, comprising:
receiving, from a measurement circuit of the gas sensor operably coupled to a gas sensing element of the gas sensor, dielectric excitation responses of the gas sensing element while the gas sensing element is exposed to the fluid sample;
receiving, from at least one ambient sensor of the gas sensor, ambient environmental data associated with the multi-gas analysis of the fluid sample;
receiving, from an input device of the gas sensor, contextual data associated with the multi-gas analysis of the fluid sample;
selecting, from a memory associated with the on-board, low-power data processor, one or more gas analysis models based on the received dielectric excitation responses of the gas sensing element, the received ambient environmental data, or the received contextual data, or any combination thereof;
selecting and providing, as inputs to the one or more selected gas analysis models, at least a portion of the received dielectric excitation responses to determine outputs of the one or more selected gas analysis models; and
determining a respective classification, or a respective concentration, or a combination thereof, of at least two gases in the fluid sample based on the outputs of the one or more selected gas analysis models.

14. The method of claim 13, wherein selecting the one or more gas analysis models comprises:
providing, as inputs to one or more parameter analyzers stored in the memory, at least the portion of the received dielectric excitation responses of the gas sensing element, at least a portion of the received ambient environmental data, and at least a portion of the received contextual data, or any combination thereof, to determine outputs of the one or more parameter analyzers.

15. The method of claim 13, wherein, after resolving the at least two gases in the fluid sample, the process comprises recalibrating the gas sensor by recalculating one or more new coefficient values of the one or more of the gas analysis models based on the received dielectric excitation responses.

16. The method of claim 13, wherein, after performing the multi-gas analysis of the fluid sample, the process comprises recalibrating the gas sensor by:
providing the received dielectric excitation responses to one or more other sensors of a swarm of communicatively coupled sensors;
receiving, from the one or more other sensors, one or more recalculated coefficient values of the one or more of the gas analysis models; and
storing, in the memory, the one or more recalculated coefficient values to update the one or more gas analysis models.

17. A gas sensor for multi-gas analysis of a fluid sample, comprising:
a gas sensing element configured to contact the fluid sample;
a measurement circuit operatively coupled to the gas sensing element and configured to provide dielectric excitation to, and to measure dielectric excitation responses of, the gas sensing element while the gas sensing element contacts the fluid sample;
an ambient environment sensor configured to collect ambient environmental data of an ambient environment associated with the multi-gas analysis;
an input device configured to receive contextual data associated with the multi-gas analysis; and
a data processing unit communicatively coupled to the measurement circuit, the ambient environment sensor, and the input device, wherein the data processing unit comprises a memory storing gas analysis models and an on-board, low-power data processor configured to resolve at least two gases in the fluid sample by:

receiving, from the measurement circuit, the dielectric excitation responses of the gas sensing element while the gas sensing element contacts the fluid sample;

receiving, from the input device, the contextual data associated with the multi-gas analysis of the fluid sample;

receiving, from the ambient environment sensor, the ambient environmental data associated with the multi-gas analysis of the fluid sample;

selecting, from the memory, at least one of the gas analysis models stored in the memory based at least in part on the received dielectric excitation responses of the gas sensing element, the received contextual data, or the received ambient environmental data, or any combination thereof;

selecting and providing, as inputs to the at least one selected gas analysis model, at least a portion of the received dielectric excitation responses to determine outputs of the at least one selected gas analysis model; and determining a respective classification, or a respective concentration, or a combination thereof, for the at least two gases in the fluid sample based on the outputs of the at least one selected gas analysis model.

18. The gas sensor of claim 17, wherein the measurement circuit comprises an application-specific integrated circuit (ASIC).

19. The gas sensor of claim 17, wherein the input device comprises a human interface device (HID) configured to receive at least a portion of the contextual data as user inputs.

* * * * *